(12) United States Patent
Bae et al.

(10) Patent No.: US 10,350,279 B2
(45) Date of Patent: Jul. 16, 2019

(54) METHOD FOR PREPARING DENDRITIC CELLS WITH INCREASED SPECIFIC GENE EXPRESSION, AND COMPOSITION FOR TREATING OR PREVENTING AUTOIMMUNE DISEASES, CONTAINING DENDRITIC CELLS PREPARED USING SAME

(71) Applicant: JW CREAGENE INC., Gyeonggi-do (KR)

(72) Inventors: Yong-Soo Bae, Gyeonggi-do (KR); Jun-Eui Park, Gyeonggi-do (KR); Yun-Ju Woo, Gyeonggi-do (KR); Jin-Ah Jang, Gyeonggi-do (KR)

(73) Assignee: JW CREAGENE INC., Gyeonggi-Do (KR)

( * ) Notice: Subject to any disclaimer, the term of this patent is extended or adjusted under 35 U.S.C. 154(b) by 221 days.

(21) Appl. No.: 15/320,010

(22) PCT Filed: Jun. 23, 2015

(86) PCT No.: PCT/KR2015/006337
§ 371 (c)(1),
(2) Date: Dec. 19, 2016

(87) PCT Pub. No.: WO2015/199402
PCT Pub. Date: Dec. 30, 2015

(65) Prior Publication Data
US 2017/0209557 A1    Jul. 27, 2017

(30) Foreign Application Priority Data

Jun. 23, 2014    (KR) .................. 10-2014-0076405

(51) Int. Cl.
| | |
|---|---|
| *C12N 5/071* | (2010.01) |
| *C12N 5/00* | (2006.01) |
| *C12N 5/02* | (2006.01) |
| *A61K 39/00* | (2006.01) |
| *A61K 35/12* | (2015.01) |
| *C12Q 1/68* | (2018.01) |
| *C12N 5/0784* | (2010.01) |
| *C12Q 1/6881* | (2018.01) |
| *G01N 33/569* | (2006.01) |

(52) U.S. Cl.
CPC .......... *A61K 39/0008* (2013.01); *A61K 35/12* (2013.01); *C12N 5/0639* (2013.01); *C12Q 1/68* (2013.01); *C12Q 1/6881* (2013.01); *G01N 33/56977* (2013.01); *A61K 2039/5154* (2013.01); *C12N 2501/02* (2013.01); *C12N 2501/25* (2013.01); *C12N 2501/998* (2013.01); *C12Q 2600/158* (2013.01)

(58) Field of Classification Search
None
See application file for complete search history.

(56) References Cited

U.S. PATENT DOCUMENTS

| | | |
|---|---|---|
| 5,851,756 A | 12/1998 | Steinman et al. |
| 5,866,115 A | 2/1999 | Kanz et al. |
| 5,994,126 A | 11/1999 | Steinman et al. |
| 6,274,378 B1 | 8/2001 | Steinman et al. |
| 2015/0125956 A1 | 5/2015 | Lee et al. |

FOREIGN PATENT DOCUMENTS

| | | | |
|---|---|---|---|
| EP | 0663930 B1 | 9/1998 | |
| EP | 0922758 A3 | 12/2001 | |
| KR | 10-2008-0095343 A | 10/2008 | |
| KR | 10-2010-0109099 A | 10/2010 | |
| WO | WO-2008130100 A1 * | 10/2008 | ......... A61K 39/0008 |

OTHER PUBLICATIONS

Raich-Reque et al., 2012, Eur. J. Immunol. vol. 42: 771-782.*
Felzmann eta l., 2005, Can. Immunol. Immunother. VOl. 54: 769-780.*
Boks, M., et al., IL—10-Generated Tolerogenic Dendritic Cells are Optimal for Functional Regulatory T Cell Induction—A Comparative Study of Human Clinical-Applicable DC, Clinical Immunology, 2012, pp. 332-342, vol. 142, No. 3.
Hilkens, C., et al., Tolerogenic Dendritic Cell Therapy for Rheumatoid Arthritis: Where Are We Now?, Clinical and Experimental Immunology, 2012, pp. 148-157, vol. 172, No. 2.
Thomas, R., et al., Feasibility, Safety and Clinical Effects of a Single Intradermal Administration of Autologous Tolerising Dendritic Cells Exposed to Citrullinated Peptides in Patients with Rheumatoid Arthritis, Arthritis & Rheumatism Abstract Supplement 2011 Annual Scientific Meeting, 2011, pp. S946, vol. 63, No. 10.
Yen, J., et al., Interferon Beta Inhibits Dendritic Cell Migration Through Stat-1 Mediated Transcriptional Suppression of CCR7 and Metalloproteinase 9, J. Immunol., 2010, pp. 3478-3486, vol. 184, No. 7.

(Continued)

*Primary Examiner* — Amy E Juedes
(74) *Attorney, Agent, or Firm* — Hultquist, PLLC; Steven J. Hultquist

(57) ABSTRACT

The present invention relates to a method for generating semi-mature dendritic cells by treating immature dendritic cells with the auto-antigen, cytokine, and PGE2 as a target for the treatment of autoimmune diseases, particularly rheumatoid arthritis, in which the levels of NR4A2 and/or UBASH3B at gene or protein are increased more than 2-fold compared to the immature dendritic cells In addition, the present invention relates to a cell therapeutic agent for treating or preventing autoimmune diseases, containing the semi-mature dendritic cells as an active ingredient. The present invention increases the therapeutic efficacy on rheumatoid arthritis retaining responsiveness to the same auto-antigen that being used for preparing semi-mature dendritic cells, thereby enabling cell therapy.

5 Claims, 17 Drawing Sheets
(8 of 17 Drawing Sheet(s) Filed in Color)
Specification includes a Sequence Listing.

(56) References Cited

OTHER PUBLICATIONS

Banchereau, J., et al., "Dendritic Cells and the Control of Immunity", "Nature", Mar. 19, 1998, pp. 245-252, vol. 392, Publisher: Macmillan Publishers Ltd.

Hsu, F.J., et al., "Vaccination of Patients with B-Cell Lymphoma Using Autologous Antigen-Pulsed Dendritic Cells", "Nature Medicine", Jan. 1996, pp. 52-58, vol. 2, No. 1.

Inaba, K., et al., "Dendritic Cells as Antigen Presenting Cells in Vivo", "International Reviews of Immunology", 1990, pp. 197-206, vol. 6.

Inaba, K., et al., "Dendritic Cell Progenitors Phagocytose Particulates, Including Bacillus Calmette-Guerin Organisms, and Sensitize Mice to Mycobacterial Antigens In Vivo", "Journal of Experimental Medicine", Aug. 1993, pp. 479-488, vol. 178, Publisher: The Rockefeller University Press.

Lutz, M.B., et al., "Immature, Semi-Mature and Fully Mature Dendritic Cells: Which Signals Induce Tolerance or Immunity?", "Trends in Immunology", Aug. 1, 2002, pp. 445-449, vol. 23, No. 9.

Menges, M., et al., "Repetitive Injections of Dendritic Cells Matured with Tumor Necrosis Factor Induce Antigen-specific Protection of Mice from Autoimmunity", "Journal of Experimental Medicine", Jan. 7, 2002, pp. 15-21, vol. 195, No. 1, Publisher: The Rockefeller University Press.

Steinman, R.M., "The Dendritic Cell System and its Role in Immunogenicity", "Annual Review of Immunology", 1991, pp. 271-296, vol. 9, Publisher: Annual Reviews Inc.

Note: For the non-patent literature citations that no month of publication is indicated, the year of publication is more than 1 year prior to the effective filing date of the present application.

\* cited by examiner

FIG.5A
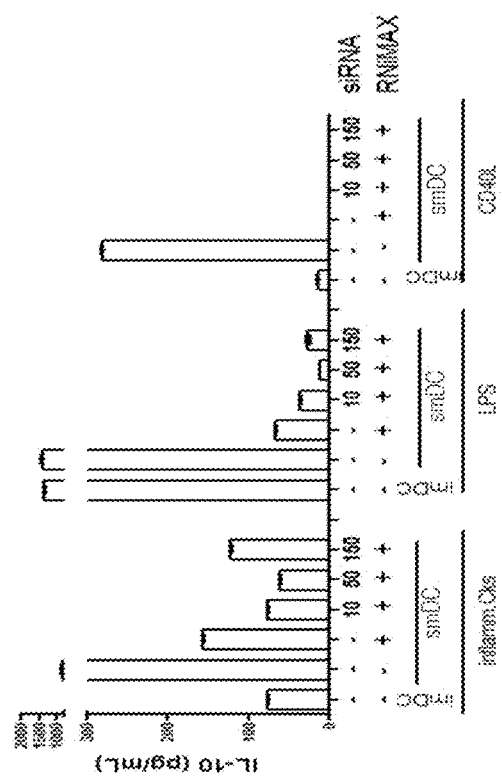
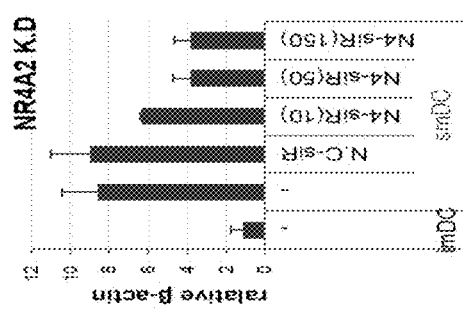

FIG.6A
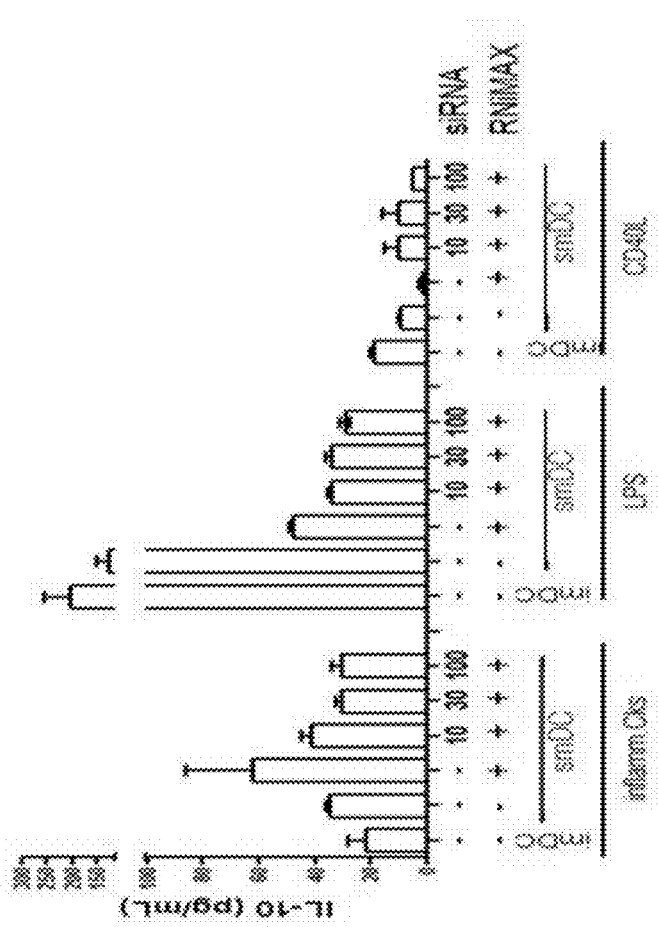
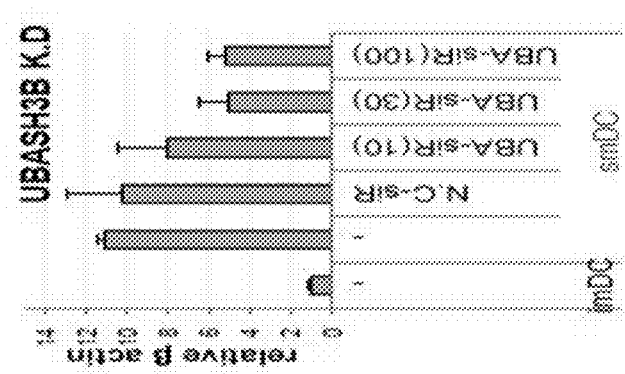

FIG.8

| Type of Dose | Patient No. | Baseline (0 week) | | | | | Clinical Effectiveness (14 weeks) | | Clinical Effectiveness (24 weeks) | |
|---|---|---|---|---|---|---|---|---|---|---|
| | | Prevalence Period (yr) | TJC/SJC (68/66) | CRP (mg/dL) | ESR (mm/hr) | Positive Ab | ACR | EULAR | ACR | EULAR |
| Forward Doses | RA-01 | 14.2 | 8/7 | 3.00 | 33.00 | 4 | ACR10 | Moderate | - | No |
| | RA-02 | 14.1 | 14/7 | 1.90 | 51.00 | 0 | - | No | - | No |
| | RA-04 | 15.5 | 28/6 | 1.90 | 36.00 | 1 | ACR40 | Moderate | <ACR10 | No |
| | RA-08 | 15.1 | 6/0 | 0.05 | 19.00 | 2 | NA* | No | NA* | Moderate |
| | RA-10 | 10.3 | 25/21 | 0.33 | 26.00 | 0 | - | No | - | No |
| | RA-13 | 15.2 | 2/0 | 0.40 | 44.00 | 0 | NA* | No | NA* | No |
| Backward Doses | RA-05 | 1.6 | 6/6 | 0.15 | 27.00 | 4 | ACR50 | Good | ACR40 | Moderate |
| | RA-06 | 40.1 | 8/0 | 0.07 | 64.00 | 2 | NA* | Moderate | NA* | Moderate |
| | RA-07 | 18.1 | 11/7 | 0.60 | 47.00 | 1 | <ACR10 | Moderate | - | No |
| | RA-09 | 21.2 | 15/4 | 0.72 | 60.00 | 2 | <ACR10 | Moderate | ACR50 | Good |
| | RA-11 | 17.6 | 10/1 | 0.03 | 65.00 | 3 | - | No | - | No |
| | RA-12 | 11.3 | 18/5 | 1.70 | 41.00 | 1 | ACR50 | Moderate | ACR50 | Good |

METHOD FOR PREPARING DENDRITIC CELLS WITH INCREASED SPECIFIC GENE EXPRESSION, AND COMPOSITION FOR TREATING OR PREVENTING AUTOIMMUNE DISEASES, CONTAINING DENDRITIC CELLS PREPARED USING SAME

CROSS-REFERENCE TO RELATED APPLICATIONS

This application is a U.S. national phase under the provisions of 35 U.S.C. § 371 of International Patent Application No. PCT/KR15/06337 filed Jun. 23, 2015, which in turn claims priority of Korean Patent Application No. 10-2014-0076405 filed Jun. 23, 2014. The disclosures of such international patent application and Korean priority patent application are hereby incorporated herein by reference in their respective entireties, for all purposes.

TECHNICAL FIELD

The present invention relates to a method for generating semi-mature dendritic cells for treatment of autoimmune diseases, particularly rheumatoid arthritis, and a composition for the treatment or prevention of autoimmune diseases, which contains, as an active ingredient, dendritic cells produced using the method.

BACKGROUND ART

Dendritic cells in the skin were first found by Langerhans in 1868, and the function thereof as immunity-enhancing cells was reported by Cohn and Steinmann in 1973. In 1990s, dendritic cells were found to function as professional antigen presenting cells (APCs), and were found to play an important role in immune activation and regulation. Dendritic cells in the human body represent only about 0.3% of total circulating leukocytes, but consist of a heterogeneous population having a phenotype differentiated from that of macrophages. Dendritic cells are differentiated in that they are professional antigen-presenting cells, unlike B cells or macrophages displaying a relatively weak antigen-presenting capability. Dendritic cells have the ability to induce a primary immune response capable of stimulating naive T cells that have not been exposed to antigen, and these dendritic cells are the only cells having the capability to induce immunological memory. It is known that dendritic cells can function to induce strong immune responses, because these dendritic cells are antigen presenting cells (APCs) that express, on the cell surface, high levels of both antigen presenting MHC molecules (I/II) and co-stimulatory molecules, for example, CD-80 and CD-86, and adhesion molecules, for example, ICAM-1, and secrete various cytokines (IFN-alpha, IL-12, IL-18, etc.). It is known that, because dendritic cells express high levels of antigen presenting molecules (HMC molecules and co-stimulatory molecules) on the cell surface, and secrete various cytokines such as IFN-alpha, IL-12 and the like, these dendritic cells can induce the generation of antigen-specific killer T cells and the proliferation and activation of Th1 cells.

As described above, dendritic cells are the strongest antigen-presenting cells. A very small number of dendritic cells are present in vivo, but these cells strongly induce T cell immunity, and thus have been studied as therapeutic agents against cancers or infectious diseases in clinical studies focusing on the induction of immunity against the specific antigens. It was found that antigen immunogenicity was triggered by adoptive transfer of dendritic cells that were isolated from tissues or blood, antigen-pulsed, and matured in vitro. Thus, these dendritic cells are highly valuable as cellular vaccines for inducing antigen-specific immunity against cancer or pathogenic microbes (Inaba, K. et al., 3. Exp. Med., 178:479, 1993; Inaba, K. et al., Int. Rev Immunol., 6:197, 1990; Hsu, F. et al., Nature Med., 2:52, 1996). Techniques for the isolation and maturation of dendritic cells are described in a number of documents, and there are various methods, including a method comprising generating mature dendritic cells from immature dendritic cells derived from pluripotent cells having the capability to express any one of the characteristics of macrophages or dendritic cells, and bringing the immature dendritic cells into contact with dendritic cell maturation factors including IFN-α (European Patent No. 922,758); a method comprising culturing human CD34+ hematopoietic cells with (i) GM-CSF, (ii) TNF-α and IL-3 and/or (iii) GM-CSF and TNF-α to induce the formation of CD1a+ hematopoietic cells, and recovering the CD1a+ human dendritic cells from the culture (European Patent No. 663,930); and a method comprising isolating peripheral blood cells, enriching blood progenitor cells expressing CD34 antigen, and culturing the cells with a combination of hematopoietic growth factors and cytokines (WO 95/28479).

However, prior art documents and patents are merely directed to methods of generating dendritic cells by sensitizing immature dendritic cells with non-specific antigen, and do not teach a method of generating semi-mature dendritic cells by sensitizing immature dendritic cells with a specific selected self-antigen(autoantigen).

Accordingly, based on the function of antigen-specific semi-mature dendritic cells in immune-tolerance, the present inventors have found that semi-mature dendritic cells can be developed from immature dendritic cells pulsed with self-antigens selected among the overexpressed self-antigens in patients with rheumatoid arthritis. These semi-mature dendritic cells increase the expression of a specific gene and mediate immune tolerance to the selected self-antigens (autoantigen) and thus improve therapeutic efficacy on rheumatoid arthritis.

DISCLOSURE OF INVENTION

Technical Problem

It is an object of the present invention to provide a method of generating semi-mature dendritic cells having increased expression of a specific gene after pulsing immature dendritic cells with a specific self-antigen(autoantigen).

Another object of the present invention is to provide a cell therapeutic agent that contains semi-mature dendritic cells generated by the method described above, and increases the therapeutic efficacy on an autoimmune disease by inducing immune tolerance to the same self-antigen(autoantigen) used for semi-mature dendritic cell generation, and a method for preparing the cell therapeutic agent.

Still another object of the present invention is to provide a method for measuring an expression level of a gene or a protein, which is specifically increased by treatment with a specific self-antigen(autoantigen).

Technical Solution

To achieve the above objects, the present invention provides a method for generating semi-mature dendritic cells comprising a step of treating the immature dendritic cells with the self-antigen(autoantigen), a cytokine and prostaglandin E2 (PGE2), wherein the semi-mature dendritic cells have at least 2-fold increased expressions of NR4A2 and/or UBASH3B at gene or protein level compared to immature dendritic cells.

The present invention also provides a cell therapeutic agent for treatment of an autoimmune disease by inducing tolerance to the same self-antigen(autoantigen) used for semi-mature dendritic cell generation as described above, the cell therapeutic agent containing, as an active ingredient, the semi-mature dendritic cells.

The present invention also provides a method for preparing a cell therapeutic agent for prevention or treatment of autoimmune disease, the cell therapeutic agent containing semi-mature dendritic cells, the method comprising the steps of:

(a) treating immature dendritic cells with an self-antigen (autoantigen), a cytokine and prostaglandin E2 (PGE2) to produce semi-mature dendritic cells;

(b) confirming that expression of NR4A2 and/or UBASH3B protein or a gene encoding the protein in the semi-mature dendritic cells increased at least 2-fold compared to expression of the NR4A2 and/or UBASH3B protein or the protein-encoding gene in immature dendritic cells; and (c) preparing a cell therapeutic agent containing the semi-mature dendritic cells in which the expression of the NR4A2 and/or UBASH3B protein or the protein-encoding gene increased at least 2-fold.

The present invention also provides a method for measuring an expression level of NR4A2 and/or UBASH3B protein or a gene encoding the protein in semi-mature dendritic cells for the prevention or treatment of autoimmune disease, the method comprising the steps of:

(a) treating immature dendritic cells with an self-antigen (autoantigen), a cytokine and PGE2 to produce semi-mature dendritic cells;

(b) measuring the expression level of the NR4A2 and/or UBASH3B protein or the protein-encoding gene in the immature dendritic cells;

(c) measuring the expression level of the NR4A2 and/or UBASH3B protein or the protein-encoding gene in the produced semi-mature dendritic cells; and (d) comparing the expression levels of the NR4A2 and/or UBASH3B protein or the protein-encoding gene, measured in step (b) and step (c).

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 5A shows experimental results indicating that NR4A2 gene expressed in semi-mature dendritic cells according to a production method of the present invention regulates IL-10 secretion.

FIG. 6A shows experimental results indicating that semi-mature dendritic cells according to a production method of the present invention induce T-cell immune tolerance by IL-10 secretion, and experimental results indicating IL-10 secretion levels of semi-mature dendritic cells under various stimulation conditions.

FIG. 8 shows the clinical effectiveness of semi-mature dendritic cells for 14 weeks and 24 weeks on 12 patients administered five times with semi-mature dendritic cells in varying doses (NA: patient in which the swollen joint count is 0 at the baseline time, and thus ACR evaluation is impossible).

BEST MODE FOR CARRYING OUT THE INVENTION

Figure 1A:
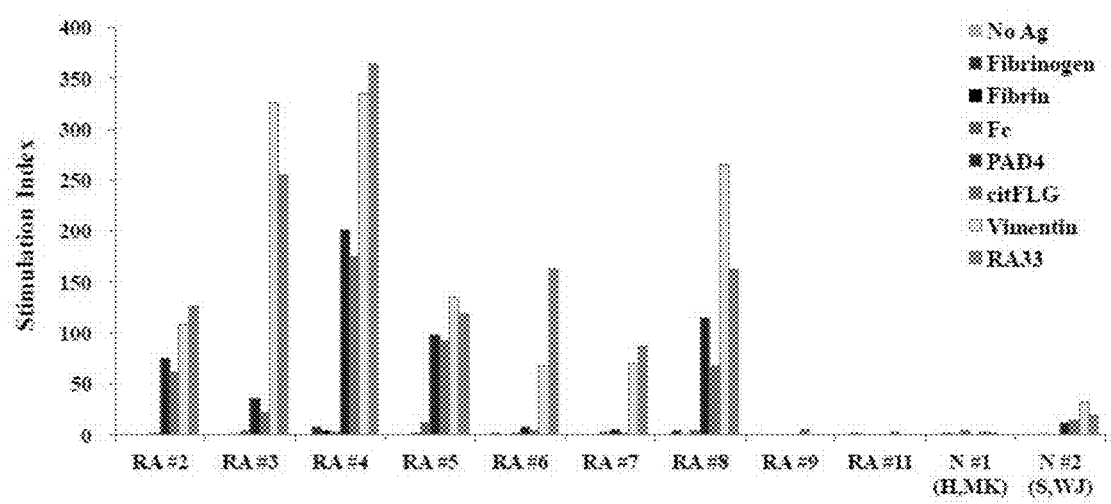
FIG. 1A shows the results of an experiment performed to measure T-cell responses (IFN-γ) to self-antigens(autoantigens) using the blood of normal persons and rheumatoid arthritis patients in order to select a specific self-antigen (autoantigen) to be used to sensitize semi-mature dendritic cells.

Unless defined otherwise, all technical and scientific terms used herein have the same meaning as commonly understood by one of ordinary skill in the art to which the invention pertains. Generally, the nomenclature used herein and the experiment methods, which will be described below, are those well known and commonly employed in the art.

In one aspect, the present invention is directed to a method for generating semi-mature dendritic cells in which expression of NR4A2 and/or UBASH3B protein or a gene encoding the protein is increased at least 2-fold compared to that in immature dendritic cells, the method comprising a step of treating the immature dendritic cells with an self-antigen(autoantigen), a cytokine and prostaglandin E2 (PGE2).

In an example of the present invention, immature dendritic cells produced by differentiation of peripheral blood monocytes (PBMCs) from normal persons or rheumatoid arthritis patients were treated with a selected specific self-antigen(autoantigen), a cytokine and prostaglandin E2 (PGE2), thereby generating semi-mature dendritic cells.

As used herein, the term "dendritic cells" are meant to include a population of dendritic cells, and refers to professional antigen presenting cells that absorb and treat an antigen and present the treated antigen together with a MHC (major histocompatibility complex) class I complex or a MHC class II complex. Dendritic cells that are used in the present invention refer to cells having the typical phenotype and characteristics of dendritic cells disclosed in Steinman et al., Annual Rev. Immunol. 9:271-296, 1991 and Banchereau and Steinman Nature 392:245-252, 1998. Dendritic cells include both immunogenic and tolerogenic antigen presenting cells, and are classified into immature dendritic cells (imDCs), semi-mature dendritic cells (smDCs), and mature dendritic cells (mDCs).

As used herein, the term "immature dendritic cells (imDCs)" refers to dendritic cells which do not express cell surface markers such as CD14, like mature dendritic cells, and which express CCR7 and cytoplasmic protein DC-LAMP at low levels, express co-simulatory molecules (CD40, CD80 and CD86) at low levels, and express CD1a, CCR1, CCR2, CCR5 and CXCR1 at conventional levels.

As used herein, the term "mature dendritic cells (mDCs)" refers to cells formed by maturation of immature dendritic cells. Mature dendritic cells show increased expression of not only DC-LAMP, but also MHC class II, CD40, CD80, CD83 and CD86, release proinflammatory cytokines, and induce increased proliferation of allogeneic T cells and syngeneic T cells in a mixed lymphocyte reaction and/or increased production of dendritic cell cytokines. The mature dendritic cells (mDCs) express CCR7 and CXCR4 at high levels.

As used herein, the term "semi-mature dendritic cells (smDCs)" refers to dendritic cells that lack some of the characteristics of immature dendritic cells, have some of the phenotypes of mature dendritic cells, and show partially or incompletely maturated morphological and phenotypic characters. Semi-mature dendritic cells generally have the capability to induce an immune tolerance response to an self-antigen(autoantigen).

According to a preferred embodiment of the present invention, monocytes are obtained from normal persons or rheumatoid arthritis patients, and then the cells are primarily cultured using a medium (preferably a medium supplemented with GM-CSF) on a suitable substrate. Substances that promote differentiation of pluripotent cells or multipotent cells into immature dendritic cells, particularly GM-CSF, are disclosed in U.S. Pat. Nos. 5,851,756 and 5,994,126, the contents of which are incorporated herein by reference. The substrate is preferably a substrate to which cells can adhere. More preferably, the substrate is a plastic substrate which is used in tissue culture.

In addition to GM-CSF, factors that prevent or inhibit proliferation of non-dendritic cells may be added to the culture medium for improving yield of immature dendritic cells. The factors include, for example, IL-4 and/or IL-13 which inhibits macrophages. While the factors promote the proliferation of dendritic progenitor cells, they inhibit the growth of non-dendritic cells to thereby increase the number of immature dendritic cells in the medium.

The self-antigen(autoantigen) that is used in the present invention may be, for example, one or more selected from the group consisting of α-enolase, filaggrin, PAD4 (peptidyl arginine deiminase 4), RA33 (heterogeneous nuclear ribonucleoprotein A2), fibrinogen-α, fibrinogen-β, collagen II, histone B, aggrecan, fibrin, rheumatoid factor, GPI (glucose-6-phosphate isomerase), and vimentin peptides and proteins, and citrullinated peptides and proteins thereof.

According to a preferred embodiment of the present invention, peripheral blood monocytes extracted from 9 rheumatoid arthritis patients showing an effective ELISPOT response or 2 normal persons were sensitized with respective seven antigens, including citrullinated filaggrin (JW CreaGene), PAD4 (JW CreaGene), RA33 (JW CreaGene), vimentin (JW CreaGene), fibrinogen (Sigma-Aldrich), fibrin (Sigma-Aldrich), IgGFc (Cell Science), and a certain self-antigen(autoantigen) showing an autoreactive T cell responsiveness of 50% or more was screened. In addition, on 100 Korean rheumatoid arthritis patients, 9 autoantibodies, including citrullinated or non-citrullinated filaggrin (JW CreaGene), PAD4 (JW CreaGene), RA33 (JW CreaGene), vimentin (JW CreaGene), fibrinogen (Sigma-Aldrich), fibrin (Sigma-Aldrich), IgG Fc (Cell Science), GPI (JW CreaGene) and collagen (Genway), were screened, and a specific self-antigen(autoantigen) was screened by using a method measuring antigen-antibody reactivity based on a case showing an OD value that is at least 1.5 times higher than that of normal persons regarded as positive.

As a result, it could be seen that self-antigens(autoantigens), which show an antigen-antibody reactivity of 30% or higher (FIG. 1A) and to which peripheral blood monocytes secreting IFN-γ shows a responsiveness of 50% or higher (FIG. 1B), were citrullinated filaggrin, PAD4 (peptidyl arginine deiminase 4), RA33 (heterogeneous nuclear ribonucleoprotein A2) and vimentin.

Thus, in the present invention, the specific self-antigen (autoantigen) that is used to treat immature dendritic cells may be one or more selected from the group consisting of citrullinated filaggrin, PAD4 (peptidyl arginine deiminase 4), RA33 (heterogeneous nuclear ribonucleoprotein A2) and vimentin.

In the present invention, self-antigen(autoantigen)-specific semi-mature dendritic cells may be produced by bring the specific antigen and the cells into "contact" with each other for a sufficient time and under sufficient conditions to enable the specific antigen to be presented from the cell surface by the semi-mature dendritic cells. Preferably, the "contact" is "co-culture".

The co-culture is preferably performed for 3-10 hours, more preferably 3-8 hours, most preferably 3-4 hours. The concentration of PEG2 used to treat the cells is preferably 0.01-5 μg/mL, and most preferably 0.5-5 μg/mL. The cytokine may be TNF-α (tumor necrosis factor-alpha), and is used at a concentration of 1-20 ng/ml, preferably 5-15 ng/ml.

It was confirmed that the semi-mature dendritic cells according to the present invention increased expression of NR4A2 and/or UBASH3B protein or a gene encoding the protein. Alternatively, the expression of PTGS2 and/or IDO protein or a gene encoding the protein in the semi-mature dendritic cells according to the present invention may further be increased, and in this case, the expression may be increased by at least twice that in immature dendritic cells.

The NR4A2 protein, a transcription factor, can bind to the promoter and enhancer of Foxp3 to act together with other transcription factors, thereby inducing Treg differentiation of CD4+ T and finally inducing anti-inflammatory responses. In addition, it is known that dopaminergic neurons are damaged by inflammatory environments to cause Parkinson's disease, and regulated expression of NR4A2 in glias and astrocytes can provide neuron protective effects, by inhibiting the secretion of TNF-α, IL-1β, NO and ROS.

The UBASH3B protein has a PGM-like domain in the C-terminal region, is evolutionally similar to PGM/AcP enzyme, and has phosphorylase activity. This UBASH3B protein can dephosphorylate activated Src tyrosine kinase (phosphorylated) of T cells, resulting in negative regulation of T cells.

MLN-DCs that express the PTGS2 protein interfere with Th2 differentiation and play an important role in the development of Treg. When DCs are treated with IV IG, the secretion of PGE2 from the DCs can increase, and the expression of Cox2 in the DCs can increase while the expression of Treg can also increase to reduce EAE scores.

The IDO protein is an enzyme functioning as indoleamine 2,3-dioxygenase, and is involved in degradation of the essential amino acid L-tryptophan.

In the present invention, NR4A2 gene (NM_006186: SEQ ID NO: 11), UBASH3B gene (NM_032873: SEQ ID NO: 12), PTGS2 gene (NM_000963: SEQ ID NO: 13), and IDO gene (NM_002164: SEQ ID NO: 14) mean genes that encode NR4A2 protein, UBASH3B protein, PTGS2 protein, and IDO protein, respectively.

The expression of the protein can be measured by an analysis method, such as Western blotting, ELISA, radioimmunoassay analysis, radial immunodiffusion, tissue immunohistochemistry, immunoprecipitation assay, complement fixation assay, or FACS, and the expression of the gene may be measured by PCR, real-time PCR or RT PCR, but is not limited thereto.

Figure 2A:
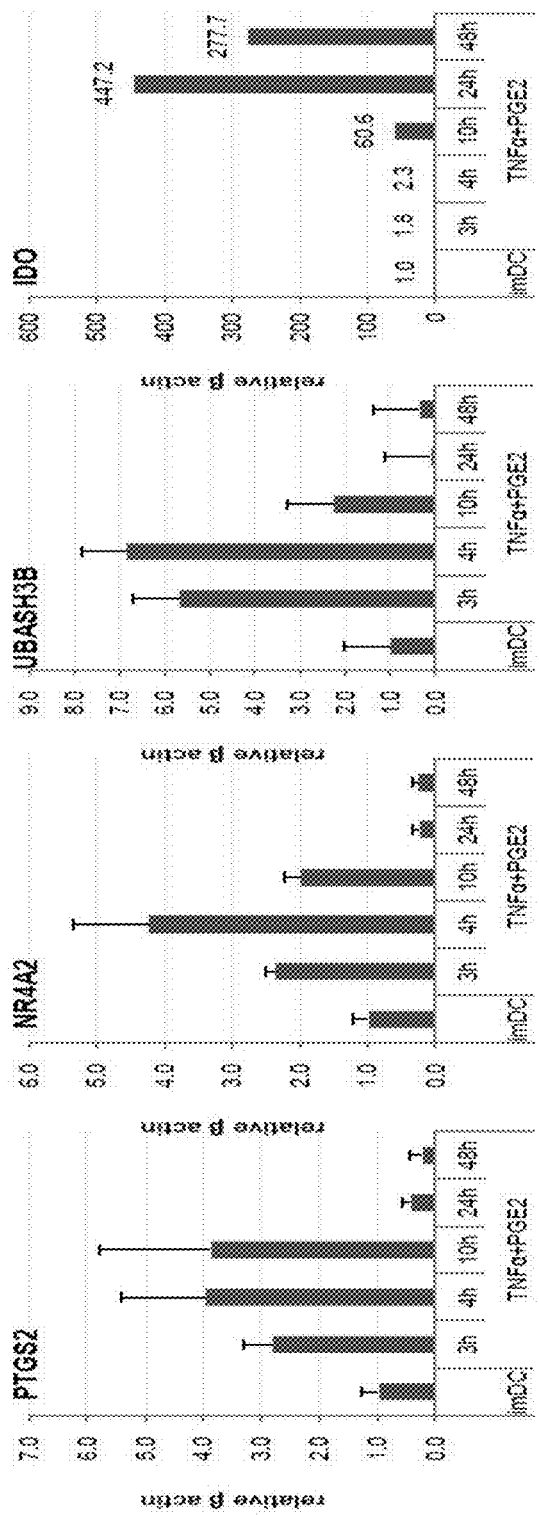
FIG. 2A shows experimental results indicating the expression levels of specific genes as a function of time of treatment with TNF-α+PGE2.
Figure 2B:
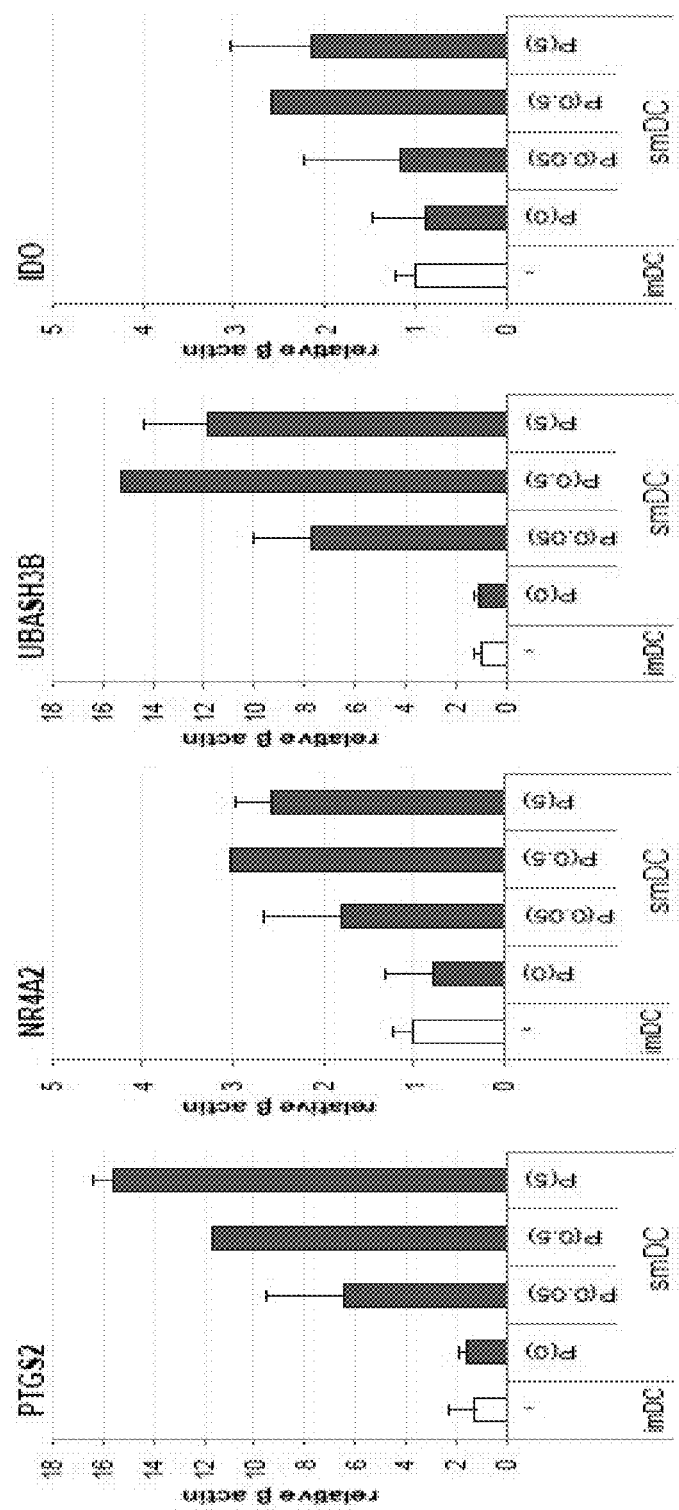
FIG. 2B shows experimental results indicating the expression levels of specific genes as a function of the concentration of PGE2.

In an example of the present invention, expression of a specific gene in the semi-mature dendritic cells of the present invention was measured by real-time PCR. As a result, it could be confirmed that, when the concentration of PGE2 used for treatment of the cells was 0.01-5 μg/mL, expression of NR4A2 and/or UBASH3B protein or a gene encoding the protein in the semi-mature dendritic cells increased at least 2-fold compared to that in immature dendritic cells. In addition, it could be found that expression of PTGS2 and/or IDO gene in the semi-mature dendritic cells increased, for example, at least twice. Specifically, it could be found that the semi-mature dendritic cells of the present invention showed an at least 2-fold increase in expression of NR4A2 gene, an at least 5-fold increase in expression of UBASH3B gene, an at least 4-fold increase in expression of PTGS2 gene, and an at least 2-fold increase in expression of IDO gene, compared to mature dendritic cells (FIGS. 2A and 2B).

Meanwhile, in order to confirm the characteristics of the semi-mature dendritic cells of the present invention and to find the reason why the semi-mature dendritic cells of the present invention exhibit excellent therapeutic effects in rheumatoid arthritis patients compared to conventional therapeutic agents, it is important to measure the characteristically increased expression level of a specific gene in the semi-mature dendritic cells of the present invention.

Therefore, in another aspect, the present invention provides a method for measuring an expression level of NR4A2 and/or UBASH3B protein or a gene encoding the protein in semi-mature dendritic cells for the prevention or treatment of autoimmune disease, the method comprising the steps of:

(a) treating immature dendritic cells with an self-antigen (autoantigen), a cytokine and PGE2 to produce semi-mature dendritic cells;

(b) measuring the expression level of the NR4A2 and/or UBASH3B protein or the protein-encoding gene in the immature dendritic cells;

(c) measuring the expression level of the NR4A2 and/or UBASH3B protein or the protein-encoding gene in the produced semi-mature dendritic cells; and (d) comparing the expression levels of the NR4A2 and/or UBASH3B protein or the protein-encoding gene, measured in step (b) and step (c).

In the present invention, measurement of the expression level of the protein or the gene may be performed using a conventional method, and specific examples of this method are as mentioned above. In the present invention, measurement of the expression level of the protein or the gene may be performed, for example, by amplifying specific genes using a primer pair selected from among primers of SEQ ID NOs: 1 to 10, measuring the expression levels of the specific genes by real-time PCR, normalizing the expression levels with β-actin, and analyzing relative values, which is resulted from dividing the normalized expression levels by expression levels measured in immature dendritic cells. β-actin is the main component of the cytoskeleton, is expressed uniformly in most cells, is not easily changed by external conditions in nature thereof, and shows a certain high expression level. Such genes are referred to as housekeeping genes, and are used as reference values to compare the expression levels of specific genes. In an example of the present invention, using the expression level of β-actin as a reference value, the expression level of NR4A2 and/or UBASH3B gene in semi-mature dendritic cells was measured and divided by the expression level of NR4A2 and/or UBASH3B gene in immature dendritic cells used as a control group. As a result, it could be seen that, when the concentration of PGE2 used for treatment of the cells was 0.05-5 μg/mL, the expression levels of the NR4A2 and UBASH3B genes increased at least 2-fold and 5-fold, respectively, compared to those in immature dendritic cells.

In addition, the method of the present invention may further comprise measuring the expression level of PTGS2 and/or IDO gene.

The concentration of PGE2 used for treatment of the cells may be 0.05-5 μg/ml, and the time required to treat the immature dendritic cells with PGE2, the self-antigen(autoantigen) and the cytokine may be 3-10 hours. The self-antigen(autoantigen) may be one or more selected from the group consisting of (citrullinated filaggrin, PAD4 (peptidyl arginine deiminase 4), RA33 (heterogeneous nuclear ribonucleoprotein A2), and vimentin. The cytokine is TNF-α (tumor necrosis factor-alpha).

In addition, according to a preferred embodiment, a disease or disorder to which the composition of the present invention is applied may be rheumatoid arthritis, but is not necessarily limited thereto. In other words, an autoimmune disease that can be treated with the composition comprising the semi-mature dendritic cells of the present invention includes any disease or disorder caused by an autoimmune response in vivo. Examples of the autoimmune disease include type 1 diabetes, rheumatoid arthritis, celiac disease, IgA deficiency, Crohn's disease, multiple sclerosis, systemic lupus erythematosus, Sjogren's syndrome, scleroderma, polymyositis, chronic active hepatitis, mixed connective tissue disease, primary biliary cirrhosis, pernicious anemia, autoimmune thyroiditis, idiopathic Addison's disease, vitiligo, gluten-sensitive enteropathy, Grave's disease, myasthenia gravis, autoimmune neutropenia, idiopathic thrombocytopenic purpura, cirrhosis, pemphigus vulgaris, autoimmune infertility, goodpastures syndrome, bullous pemphigoid, discoid lupus erythematosus, ulcerative colitis, dense deposits disease, and the like.

In another example of the present invention, in order to confirm the clinical effect of the semi-mature dendritic cells of the present invention, semi-mature dendritic cells sensitized with specific self-antigens(autoantigens) were administered to 12 active rheumatoid arthritis patients. The patients were divided into two groups, each consisting of 6 persons, and then the cells were administered subcutaneously to each group at a concentration of $5 \times 10^6$ cells/0.5 mL or $1.5 \times 10^7$ cells/1.5 mL. The cells were administered a total of three times at 2-week intervals up to the first 4 weeks, and then administered a total of twice at 2-week intervals after a drug holiday of 4 weeks. Thus, the cells were administered for a total of 10 weeks. Before and after administration and at 8 and 14 weeks after administration, blood was sampled from the rheumatoid arthritis patients, and the reactivities of autoantibodies and T cells in the blood were measured.

Figure 10:
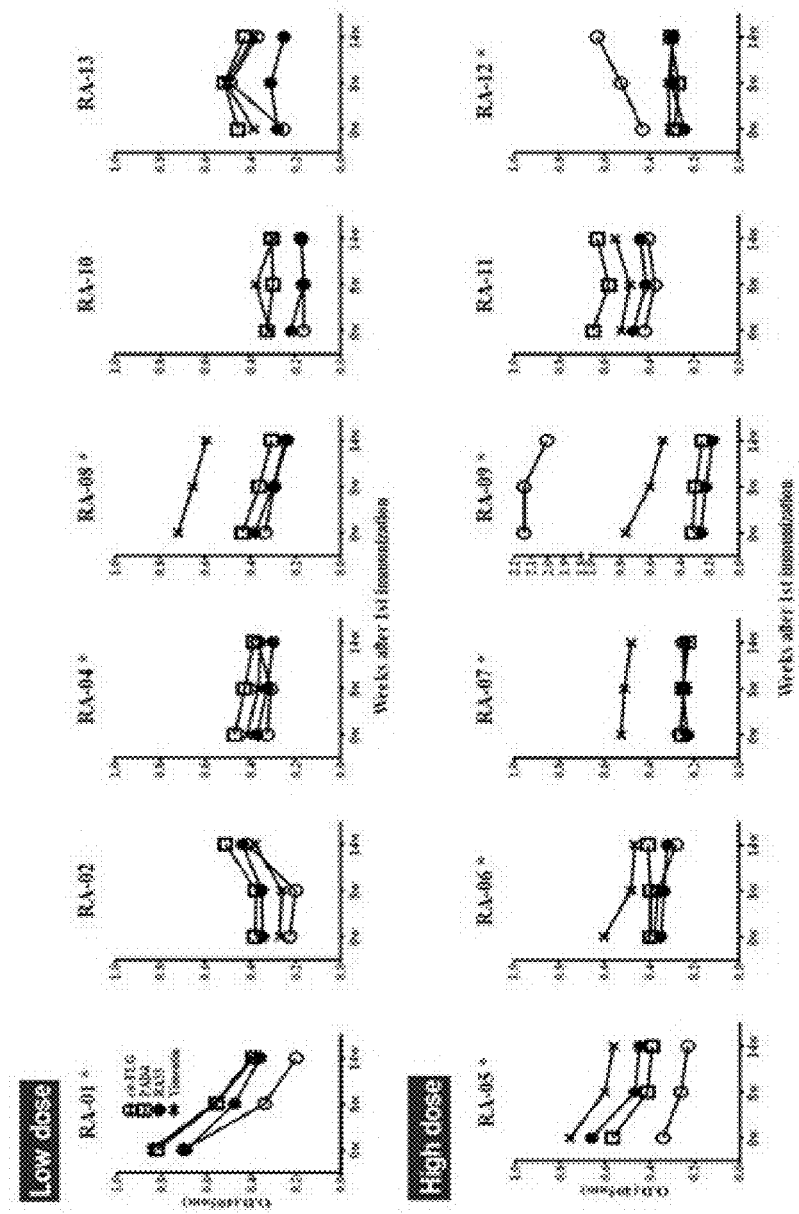
FIG. 10 shows experimental results indicating the decreases in specific autoantibodies (citrullinated filaggrin, PAD4, RA33, and vimentin) in 12 patients at 14 weeks after administration of semi-mature dendritic cells.
Figure 11:
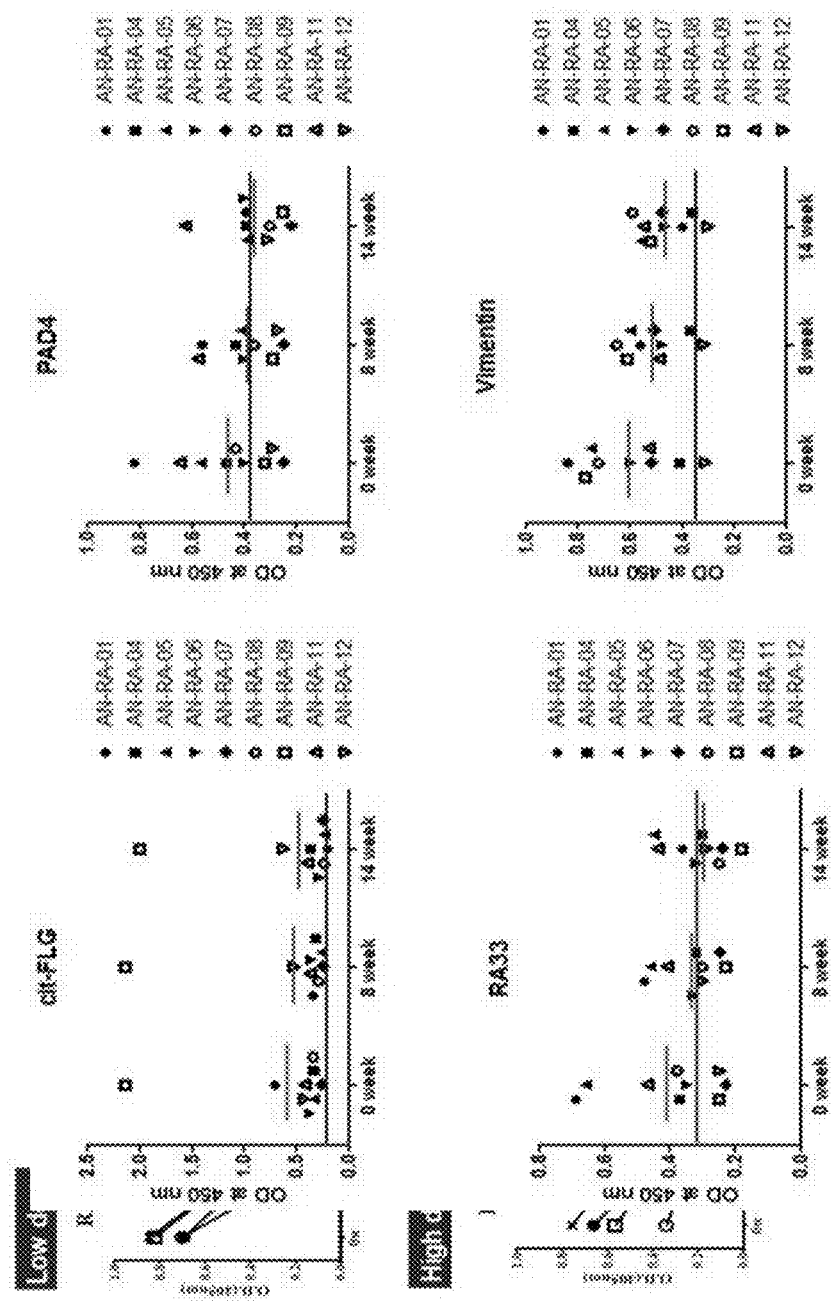
FIG. 11 shows experimental results indicating the time-dependent decreases in autoantibodies (citrullinated filaggrin, PAD4, RA33, and vimentin), measured at 14 weeks after semi-mature dendritic cells to 9 patients having one or more self-antigen(autoantigens).

As a result, it could be found that autoantibodies against specific self-antigens (autoantigens: citrullinated filaggrin, PAD4, RA33, and vimentin) decreased (FIGS. 10 and 11).

Therefore, in another aspect, the present invention provides a cell therapeutic agent for treatment of an autoimmune disease having responsiveness to the same self-antigen (autoantigen) as an self-antigen(autoantigen) used for treatment of semi-mature dendritic cells produced by the method of the present invention, the cell therapeutic agent containing, as an active ingredient, the semi-mature dendritic cells.

As used herein, the term "cell therapeutic agent" refers to a drug used for treatment, diagnosis and prevention of diseases through a series of processes including the process of changing a cell's biological property by growing or selecting autologous, allogenic, and xenogenic cells outside the body or using other methods. The U.S. and Korea have controlled the cell therapeutic agent as a drug since 1993 and 2002, respectively. Such a cell therapeutic agent can be largely classified into two types: "a stem cell therapeutic agent" for the regeneration of tissues and the recovery of organ functions and "an immunocyte therapeutic agent" for the regulation of immune reaction, including the inhibition of immune reaction in-vivo or the accentuation of immune reaction.

The cell therapeutic agent composition of the present invention may comprise a therapeutically effective amount of a cell therapeutic agent for the treatment of diseases. As used herein, the term "therapeutically effective amount" is refers to an amount of an active ingredient or a pharmaceutical composition that induces a biological or medical reaction in tissue systems, animals, or humans, and is considered by researchers, veterinarians, doctors, or other clinicians. The therapeutically effective amount comprises an amount of inducing the alleviation of the symptoms of the disease or disorder being treated. It is obvious to those skilled in the art that cell therapeutic agent contained in the composition of the present invention will be changed according to a desired effect. Therefore, the optimum content of the cell therapeutic agent in the composition of the present invention can be easily determined by those skilled in the art, and may be adjusted depending on various factors including the type and severity of a disease, the contents of other components contained in the composition, the type of formulation, the patient's age, body weight, general health condition, sex and diet, administration time, administration route, the secretion rate of the composition, duration of treatment, and concurrently used medications.

In an example of the present invention, the semi-mature dendritic cells of the present invention were administered to 12 rheumatoid arthritis at a concentration of $5 \times 10^6$ cells/0.5 mL or $1.5 \times 10^7$ cells/1.5 mL. As a result, it could be seen that, when the semi-mature dendritic cells were added to the patients showing responsiveness to the specific antigen, the semi-mature dendritic cells functioned to reduce an autoantibody against the specific antigen, indicating that the cells have therapeutic effects (FIGS. 10 and 11). Thus, when the amount of the semi-mature dendritic cells, which can exhibit the highest effect in the smallest amount is determined by considering all the above-described factors, the cell therapeutic agent of the present invention contain the semi-mature dendritic cells in an amount of $5 \times 10^6$ to $1.5 \times 10^7$ cells/mL, more preferably $1.5 \times 10^7$ cells/ml.

In order to examine the correlation between the therapeutic effect of the semi-mature dendritic cells of the present invention and the specific genes that are expressed in the cells and identify the mechanism related thereto, whether or not dendritic cells secrete IL-10 and the functions of specific genes were examined IL-10, a cytokine secreted from Th2, regulatory T cells, dendritic cells and the like, is known to attack self-tissue to induce immune tolerance.

Figure 4:
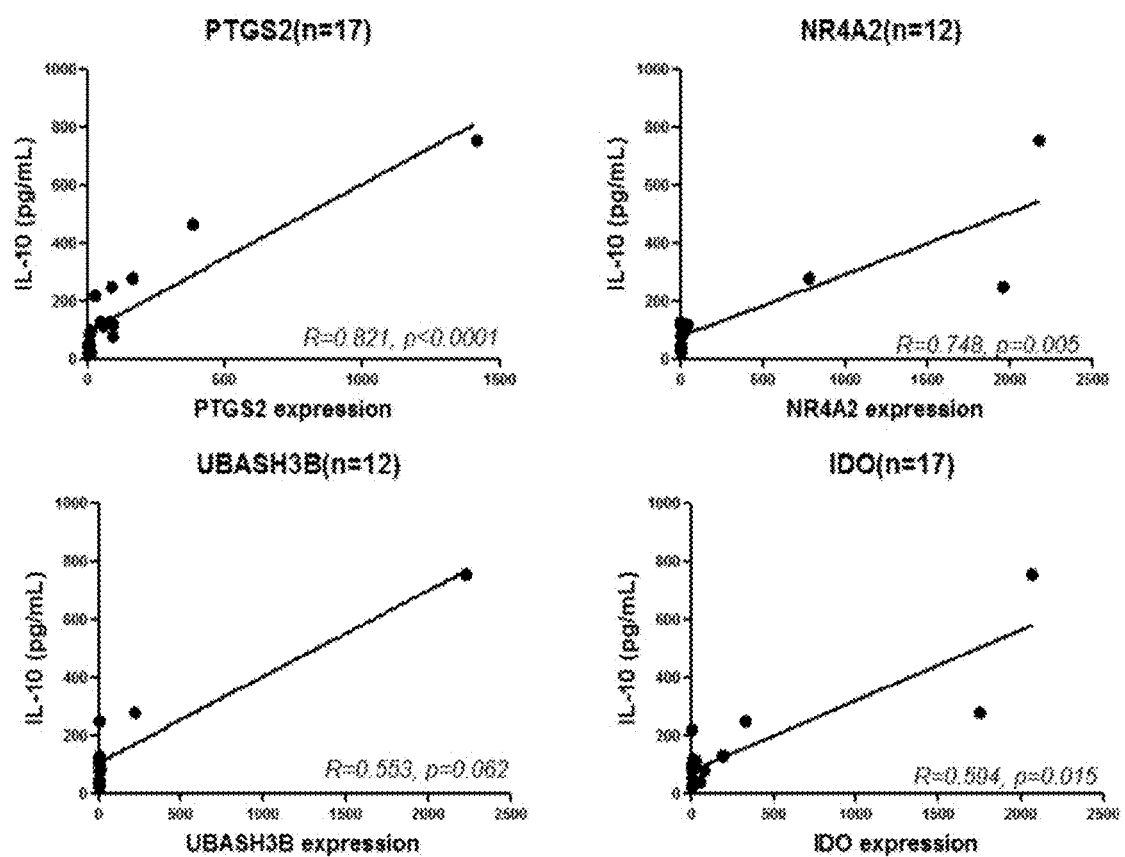
FIG. 4 shows experimental results indicating the correlation between specific gene expression and IL-10 secretion.
Figure 5B:
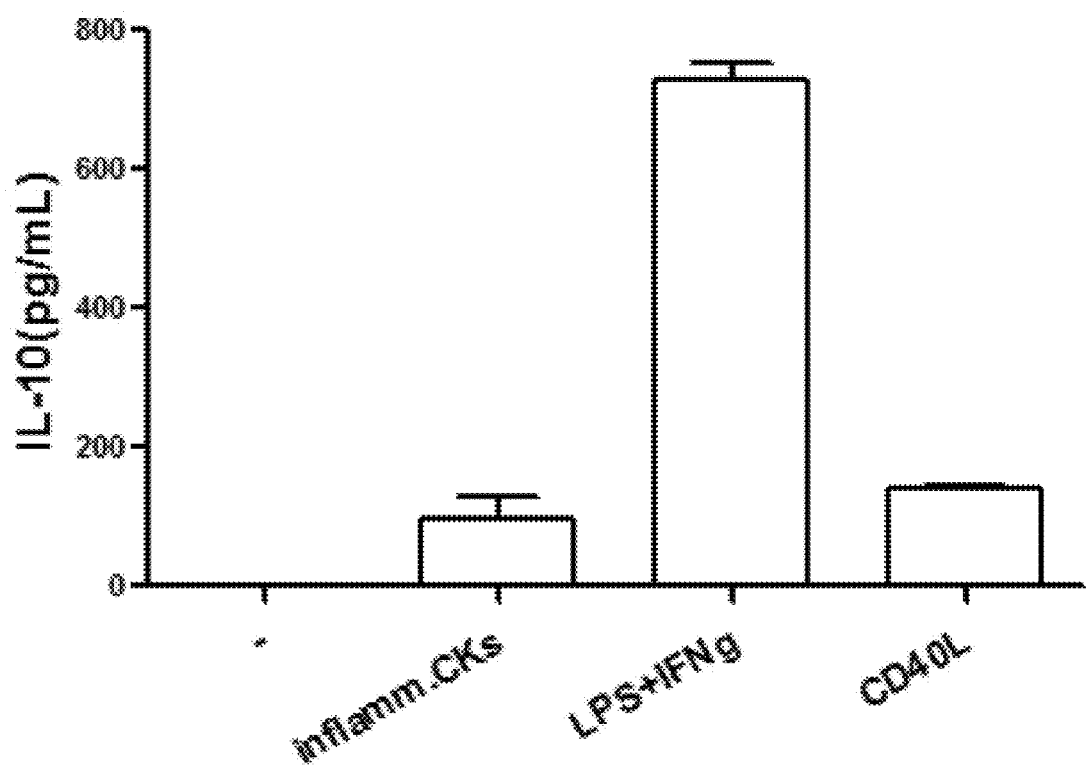
FIG. 5B shows experimental results indicating that UBASH3B gene expressed in semi-mature dendritic cells according to a production method of the present invention regulates IL-10 secretion.

In an example of the present invention, IL-10 was quantified by an ELISA kit, and as a result, it could be seen that the semi-mature dendritic cells of the present invention secreted IL-10 in a manner dependent on the time and concentration of treatment with PGE2 (FIG. 4). In another example of the present invention, based on a comparison with a control group transfected with siRNA for each gene at a concentration of 10-100 pmol (10, 50 and 100 pmol), it could be seen that the secretion of IL-10 from the semi-mature dendritic cells is attributable to specific genes, particularly NR4A2 and/or UBASH3B gene (FIGS. 5A and 5B). In addition, it could be seen that the semi-mature dendritic cells of the present invention, which show IL-10 secretion that was increased by expression of the NR4A2 and/or UBASH3B gene, was effective for treatment of rheumatoid arthritis (FIGS. 7A, 7B, and 8). In another example, it was found that the semi-mature dendritic cells of the present invention induced immune tolerance of T cells by IL-10 (FIGS. 6A, 6B, 6C, 9A, and 9B).

Therefore, the present invention provides a cell therapeutic agent for treatment of autoimmune disease, which has the effects of increasing IL-10 secretion, reducing the secretion of IFN-γ from T cells, and reducing autoantibody production.

Meanwhile, it is obvious to those skilled in the art that the semi-mature dendritic cells of the present invention may be formulated in a suitable form with a pharmaceutically acceptable carrier that is generally used in cell therapy.

Therefore, in another aspect, the present invention provides a method for preparing a cell therapeutic agent for prevention or treatment of autoimmune disease, the cell therapeutic agent containing semi-mature dendritic cells, the method comprising the steps of:

(a) treating immature dendritic cells with an self-antigen (autoantigen), a cytokine and prostaglandin E2 (PGE2) to produce semi-mature dendritic cells;

(b) confirming that expression of NR4A2 and/or UBASH3B protein or a gene encoding the protein in the semi-mature dendritic cells increased at least 2-fold compared to expression of the NR4A2 and/or UBASH3B protein or the protein-encoding gene in immature dendritic cells; and (c) preparing a cell therapeutic agent containing the semi-mature dendritic cells in which the expression of the NR4A2 and/or UBASH3B protein or the protein-encoding gene increased at least 2-fold.

In the present invention, the expression of PTGS2 or IDO protein or a gene encoding the protein in the semi-mature dendritic cells may further be increased. In this case, the expression of PTGS2 or IDO protein or the gene encoding the protein in the semi-mature dendritic cells may be increased at least 2-fold compared to that in immature dendritic cells.

In the present invention, measurement of the expression levels of specific genes may be performed by amplifying the specific genes using each primer pair selected from among primers of SEQ ID NOs: 1 to 10, measuring the expression levels of the specific genes by real-time PCR, normalizing the expression levels with β-actin, and dividing the normalized expression levels by expression levels measured in immature dendritic cells, thereby determining relative values. Specifically, the expression level of NR4A2 or UBASH3B gene in the semi-mature dendritic cells is measured using as a reference value the expression level of β-actin, a kind of housekeeping gene which is not easily changed by external conditions and shows a certain high expression level, and the measured expression level is divided by the expression level of the NR4A2 or UBASH3B gene in immature dendritic cells used as a control group. As a result, it could be seen that, when the concentration of PGE2 used for treatment of the cells was 0.05-5 µg/mL, the expression levels of the NR4A2 and UBASH3B genes in the semi-mature dendritic cells increased at least 2-fold and at least 5-fold, respectively, compared to those in immature dendritic cells. When the expression levels were measured by the above-described method, it could be seen that, when the concentration of PGE2 used for treatment of the cells was 0.05-5 µg/mL, the expression levels of PTGS2 and IDO genes in the semi-mature dendritic cells increased at least 4-fold and at least 2-fold, respectively, compared to those in immature dendritic cells.

A pharmaceutically acceptable carrier necessary for formulation of the cell therapeutic agent of the present invention refers to a composition that is physiologically acceptable and does not cause gastric disorder, allergic reactions such as gastrointestinal disorder or vertigo, or similar reactions, when administered to humans. Examples of the pharmaceutically acceptable carrier include carriers for parenteral administration, such as water, suitable oil, saline solution, aqueous glucose, and glycol. The composition of the present invention may further comprise a stabilizer and a preservative. Suitable stabilizers include antioxidants, such as sodium bisulphite, sodium sulphite and ascorbic acid. Suitable preservatives include benzalkonium chloride, methyl- or propyl-paraben, and chlorobutanol. Other pharmaceutically acceptable carriers can be found in Remington's Pharmaceutical Sciences, 19th ed., Mack Publishing Company, Easton, Pa., 1995.

In the process of preparing the cell therapeutic agent for prevention or treatment of autoimmune disease according to the present invention, the time required to treat the cells with the self-antigen(autoantigen), the cytokine and PGE2 may be 3-10 hours. Herein, the self-antigen(autoantigen) may be, for example, one or more selected from the group consisting of α-enolase, filaggrin, PAD4 (peptidyl arginine deiminase 4), RA33 (heterogeneous nuclear ribonucleoprotein A2), fibrinogen-α, fibrinogen-β, collagen II, histone B, aggrecan, fibrin, rheumatoid factor, GPI (glucose-6-phosphate isomerase), and vimentin peptides and proteins, and citrullinated peptides and proteins thereof, and the cytokine may be TNF-α (tumor necrosis factor-alpha).

EXAMPLES

Hereinafter, the present invention will be described in further detail with reference to examples. It will be obvious to a person having ordinary skill in the art that these examples are illustrative purposes only and are not to be construed to limit the scope of the present invention.

Example 1: Antigen Screening or Immune Response Monitoring by Autoantibody Identification In order to identify plasma autoantibodies present in rheumatoid arthritis (RA) patients at higher levels than those in normal persons or to monitor changes in autoplasma (immune response monitoring) after administration of semi-mature dendritic cells to RA patients, the following assay was performed. Specifically, each of a total of 9 antigens, including citrullinated or non-citrullinated filaggrin (JW CreaGene), PAD4 (JW CreaGene), RA33 (JW CreaGene), vimentin (JW CreaGene), fibrinogen (Sigma-Aldrich), fibrin (Sigma-Aldrich), IgG Fc (Cell Science), GPI (JW CreaGene) and collagen (Genway), was dispensed into a 96-well plate at a concentration of 1 µg/mL, and then after 24 hours, the plate was washed with 0.05% PBS-T and blocked with 1% BSA-containing PBS for 1 hour. After 1 hour, 50 µL of a 1:10 or 1:50 dilution of plasma from each of 100 rheumatoid arthritis patients and 14 normal persons was dispensed in duplicate, followed by incubation at room temperature for 2 hours. After 2 hours, the plate was washed with 0.05% PBS-T, and 50 µL of a 1:2000 dilution of an AP-conjugated anti-human IgG antibody (Sigma-Aldrich) in 1% BSA-containing PBS was dispensed into each well of the plate. After 1 hour, the plate was washed with 0.05% PBS-T, and 100 µL of 1 µg/mL-p-nitrophenyl phosphate (Sigma-Aldrich) was dispensed into each well of the plate. After color development, 50 µL of 0.2M sodium hydroxide was dispensed into each well of the plate to stop the reaction, and the absorbance of each well at 405 nm was measured by an ELISA reader.

Figure 1B:
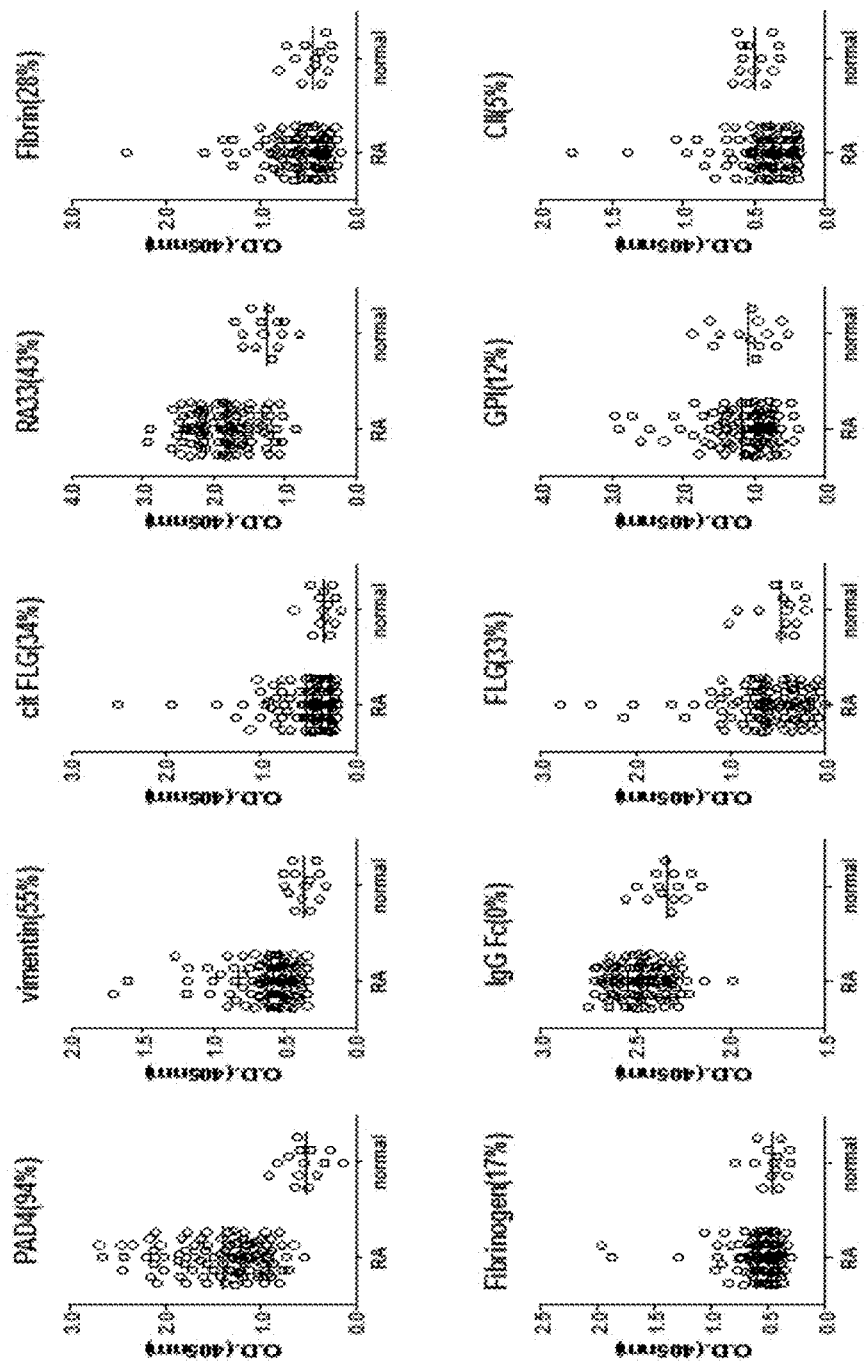
FIG. 1B shows the results of an experiment performed to measure self-antigen(autoantigen) responses to self-antigens (autoantigens) using the blood of normal persons and rheumatoid arthritis patients in order to select a specific self-antigen(autoantigen) to be used to sensitize semi-mature dendritic cells.

As a result, it could be seen that the antigen-antibody reactivity of each of citrullinated filaggrin, PAD4, RA33 and vimentin was 30% or higher (FIG. 1B). Herein, the antigen-antibody reactivity means the percentage (%) of patients having a value equal to or higher than <average absorbance of normal persons×1.5> among 100 rheumatoid arthritis patients.

Example 2: Antigen Screening and Immune Response Monitoring by IFNγ ELISPOT Assay In order to identify self-antigens(autoantigens) that increase the IFN-γ responsiveness of autoreactive T cells in the blood of rheumatoid arthritis (RA) patients compared to that in normal persons and to monitor the IFN-γ responsiveness of autoreactive T cells to self-antigens (autoantigens) (immune response monitoring) after administration of semi-mature dendritic cells to rheumatoid arthritis (RA) patients, the following assay was performed. An IFNγ-ELISPOT (BD Bioscience) assay was performed according to the manufacturer's guideline. Specifically, 100 μL of capture antibody was dispensed into each well of an ELSISPOT 96-well plate and incubated at 4° C. for 24 hours, and then the plate was blocked with 10% FBS-containing PBS for 2 hours. After blocking, 10 μg/mL of each of a total of 7 antigens, including citrullinated filaggrin (JW CreaGene), PAD4 (JW CreaGene), RA33 (JW CreaGene), vimentin (JW CreaGene), fibrinogen (Sigma-Aldrich), fibrin (Sigma-Aldrich), and IgGFc (Cell Science), was added to $2 \times 10^5$ peripheral blood monocytes (PBMCs) extracted from each of 9 rheumatoid arthritis and 2 normal persons, and then the cells were suspended in 10% human AB serum-containing RPMI1640 and dispensed into each well in duplicate. After incubation in a $CO_2$ incubator at 37° C. for 24 hours, the plate was washed with 0.05% PBS-T, and 100 μL of biotinylated detection antibody was dispensed into each well, followed by incubation at room temperature for 2 hours. After 2 hours, the plate was washed with 0.05% PBS-T, and 100 μL of a 1:100 dilution of HRP-conjugated avidin was dispensed into each well, followed by incubation at room temperature for 1 hour. After 1 hour, the plate was washed with PBS, and 100 μL of an AEC substrate (BD Biosciences) was dispensed into each well. The degree of color development was measured and compared with the degree of color development measured in a control group not treated with the self-antigen (autoantigen). The spot in each well was analyzed using an ImmunoSPOT-ELISPOT reader (Cellular Technology).

As a result, it could be seen that antigens to which peripheral blood monocytes secreting IFN-γ show a responsiveness of 50% or higher were citrullinated filaggrin, PAD4, RA33 and vimentin (FIG. 1A). IFN-γ responsiveness means the percentage (%) of patients having a value equal to or higher than <average absorbance of normal persons× 1.5> among 9 RA patients.

Considering the results of Examples 1 and 2 together, citrullinated filaggrin, PAD4, RA33 and vimentin, which show an antigen-antibody reactivity of 30% or higher and to which peripheral blood monocytes secreting IFN-γ show a responsiveness of 50% or higher, were selected as specific self-antigens(autoantigens) to be used to sensitize semi-mature dendritic cells.

Example 3: Production of Semi-Mature Dendritic Cells

A certain amount of peripheral blood monocytes extracted from normal persons or rheumatoid arthritis patients were dispensed into a plastic culture dish and cultured for 30 minutes to 1 hour, and then the floating cells were removed. The monocytes attached to the bottom were cultured in a CellGro (CellGenix) medium containing 20 ng/mL of IL-4 (JW CreaGene) and 30 ng/mL of GM-CSF (JW CreaGene) at 37° C. for 3 days, and then the suspended immature dendritic cells were collected (among these cells, some immature dendritic cells were used as a control group for confirming expression of specific genes). The collected immature dendritic cells were suspended in the CellGro medium and dispensed into a fresh plate in a certain amount, and then the cells were stimulated for 3-10 hours by addition of 5-10 μg of the self-antigens(autoantigens: JW CreaGene) selected in Examples 1 and 2, 10 ng/mL of TNFα (Peprotech) and 0.05-5 μg/mL of PGE2 (Sigma-Aldrich). The stimulated semi-mature dendritic cells were frozen with human plasma albumin (JW Pharm.) containing 5% DMSO (Sigma-Aldrich) and 5% glucose (Green Cross Corp.).

Example 4: Analysis of Expression of Specific Genes in Semi-Mature Dendritic Cells The semi-mature dendritic cells sensitized with specific self-antigens(autoantigens), obtained in Example 3, were thawed and washed with RPMI1640 (Lonza), and then mRNA was isolated from the cells using a RNeasy mini kit (Qiagen) and quantified. Then, each cDNA was synthesized from the mRNA according to the method of high capacity RNA to cDNA kit (AB). The synthesized cDNA was mixed with each primer pair of SEQ ID NOs: 1 to 10 using power SYBR green (AB), followed by real time PCR (step one plus). The expression level of each gene, normalized with β-actin, was divided by the expression level of each gene in the immature dendritic cells, thereby determining relative values.

As a result, it could be seen that, when the semi-mature dendritic cells were treated with PGE2 for 0-48 hours (particularly 3-10 hours), the semi-mature dendritic cells showed an at least 2-fold increase in expression of NR4A2 gene (NM_006186), an at least 5-fold increase in expression of UBASH3B gene (NM_032873) and an at least 3-fold increase in expression of PTGS2 gene (NM_000963), compared to the immature dendritic cells, and that expression of IDO gene (NM_002164) increased about at least 60-fold at a treatment time of 10-48 hours (FIG. 2A).

In addition, it could be seen that the semi-mature dendritic cells treated with 0.01-5 μg/mL of PGE2 showed an at least 2-fold increase in expression of NR4A2 gene (NM_006186), an at least 5-fold increase in expression of UBASH3B gene (NM_032873), an at least 4-fold increase in expression of PTGS2 gene (NM_000963) and an at least 2-fold increase in expression of IDO gene (NM_002164), compared to the immature dendritic cells (FIG. 2B).

TABLE 1

| SEQ ID NO: | Genes | | Nucleotide sequences |
|---|---|---|---|
| 1 | NR4A2 | forward: | GCC ATG CTT GGT TGT TGC AGT TCA |
| 2 | NR4A2 | reverse: | TCA TGC CAC CCA CGC AAC ATT TAG |
| 3 | UBASH3B | forward: | AAG CAA GAC TAG TGG GTG AAG CCT |
| 4 | UBASH3B | reverse: | AAA TAA GCC GGG CTC TAC ACG GAT |
| 5 | PTGS2 | forward: | GCC TAT GTG CTA GCC CAC AAA GAA |
| 6 | PTGS2 | reverse: | ACG AAG CAT CCA CAG ATC CCT CAA |
| 7 | IDO | forward: | GAT GAA GAA GTG GGG TTT GC |
| 8 | IDO | reverse: | CGC TGT GAC TTG TGG TCT GT |
| 9 | β-actin | forward: | GGC ACC CAG CAC AAT GAA GAT CAA |

TABLE 1-continued

| SEQ ID NO: | Genes | Nucleotide sequences |
|---|---|---|
| 10 | β-actin reverse: | ACT CGT CAT ACT CCT GCT TGC TGA |

Example 5: Analysis of IL-10 Secretion from Semi-Mature Dendritic Cells

According to the method of Example 3, semi-mature dendritic cells stimulated for 3-48 hours by addition of 5 μg/mL of PGE2 (Sigma-Aldrich), and semi-mature dendritic cells stimulated by addition of 0, 0.05, 0.5 and 5 μg/mL of PGE2 (Sigma-Aldrich) were thawed, and then washed using RPMI1640 (Lonza). $2 \times 10^5$ cells of the cell population were cultured in duplicate with a 10% human AB serum (Lonza)-containing RPMI1640 containing 10 ng/mL of TNFα, IL-6, IL-1β (Peprotech) or 200 units/mL of IFNγ (LG) or containing 0.1 μg/mL of LPS (Sigma-Aldrich), 200 units/mL of IFNγ (LG) or 1 μg/mL of CD40L (Peprotech), in a 96-well plate under the conditions of 37° C. and $CO_2$ for 24 hours. After 24 hours, the culture was recovered, and IL-12 and IL-10 in the culture were quantified using an ELISA kit (BD Biosciences) according to the manufacturer's a guideline.

Figure 3A:
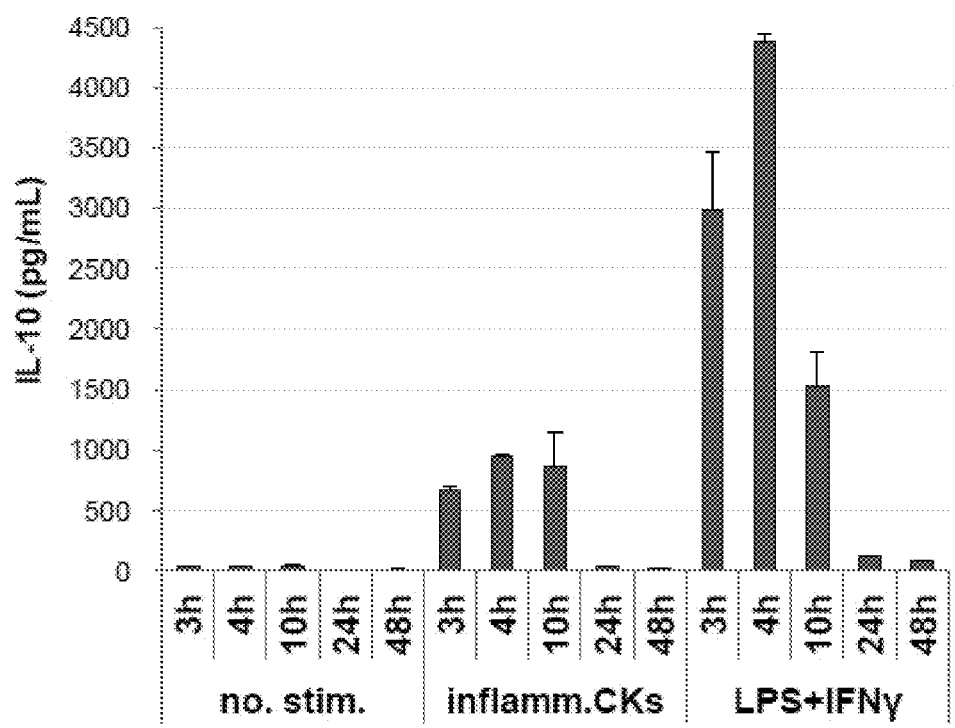
FIG. 3A shows experimental results indicating the secretion level of IL-10 as a function of the time of treatment with TNF-α+PGE2.
Figure 3B:
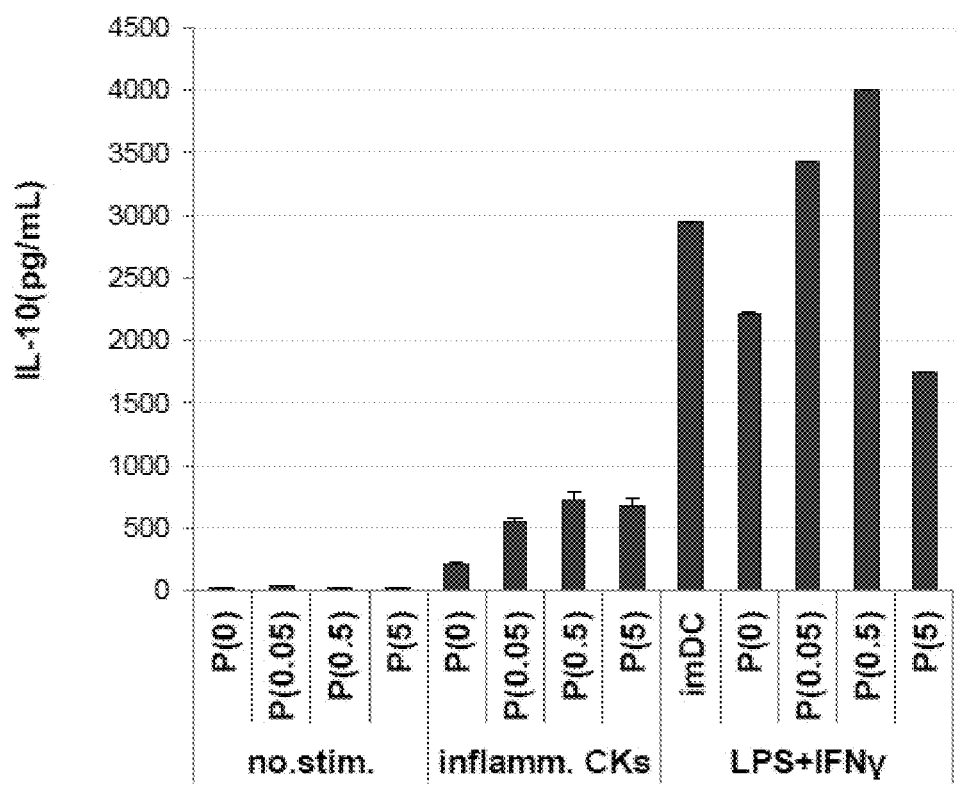
FIG. 3B shows experimental results indicating the secretion level of IL-10 as a function of the concentration of PGE2.

As a result, it could be seen that, when the semi-mature dendritic cells sensitized with PGE2 were treated with PGE2 for 3-10 hours, IL-10 secretion from the cells increased (FIG. 3A). In addition, it could be seen that, when the self-antigen(autoantigen) antigen PGE2 was used at a concentration of 0.05-5 μg/mL (corresponding to P (0.05), P (0.5) and P (5)), IL-10 secretion from the cells increased (FIG. 3B).

Example 6: siRNA Transfection for Confirming Functions of Specific Genes

In order to examine the correlation between IL-10 secreted from the semi-mature dendritic cells sensitized with a specific self-antigen(autoantigen) as confirmed in Example 5 and the expression of specific genes as confirmed in Example 4, a specific gene was knocked out by transfection with siRNA for the gene, and then changes in IL-10 secretion from the semi-mature dendritic cells and IFN-γ secretion from T cells were analyzed. Transfection of siRNA into the semi-mature dendritic cells was performed in the following manner A certain amount of human peripheral blood monocytes were dispensed into a plastic culture dish and allowed to stand for 30 minutes to 1 hour so as to adhere. Then, the floating cells were removed, and the monocytes attached to the bottom were cultured in a CellGro (CellGenix) containing 20 ng/mL of IL-4 (JW CreaGene) and 30 ng/mL of GM-CSF (JW CreaGene) for 2 days, after which the floating immature cells were collected. The immature dendritic cells suspended in the CellGro medium were dispensed at a density of $5 \times 10^5$-$10 \times 10^5$ cells/well (6-well plate). 10-100 pmol of siRNA for each of NR4A2 (Invitrogen), UBASH3B, GAPDH (positive control) and a negative control (N.C.), and 5 μL of the transporter RNAiMAX (Invitrogen) were added to 100 μL of the cultured cells which were then carefully dropped into each well and cultured for 24-36 hours. After 24 hours, the cells were stimulated for 4 hours by 5-10 μg/mL of a specific self-antigen(autoantigen) (JW CreaGene), 10 ng/mL of TNFα (Peprotech) and 5 μg/mL of PGE2 (Sigma-Aldrich), and then frozen. The produced semi-mature dendritic cells were thawed, and then cultured in a 10% human AB serum (Lonza)-containing RPMI1640 containing 10 ng/mL of TNFα, IL-6, IL-1β (Peprotech) and 200 units/mL of IFNγ (LG) or containing 0.1 μg/mL of LPS (Sigma-Aldrich) or 1 μg/mL of CD40L (Peprotech). The culture was collected, and IL-10 in the culture was quantified using an ELISA kit (BD Biosciences).

As a result, it could be seen that the specific genes expressed in the semi-mature dendritic cells of the present invention and IL-10 secretion from the cells had a high correlation (FIG. 4). Particularly, it could be seen that the NR4A2 gene regulated IL-10 secretion (FIG. 5A) and the UBASH3B gene secreted IL-10 secretion (FIG. 5B).

Example 7: Analysis of Regulation of T Cells by Semi-Mature Dendritic Cells

CD3 positive T cells with a purity of 90% or higher were separated from human peripheral blood monocytes by use of a nylon wool column, and suspended in a 10% human AB serum (Lonza)-containing RPMI1640 (Lonza) and dispensed into each well of a 48-well plate at a density of $1 \times 10^6$ cells. The semi-mature dendritic cells, produced and frozen by the method of Example 3, were thawed, washed with RPMI1640, suspended in the same medium, dispensed into each well at a density of $1 \times 10^5$ cells, and cultured under the conditions of 37° C. and $CO_2$. After 2 days, the cells were stimulated with 50 ng/mL of PMA (Sigam-Aldrich), 500 ng/mL of ionomycin (Sigam-Aldrich) and 1 μL/mL of brefeldin A (Ebioscience) for 4 hours, and the cell population was collected and subjected to FACS staining with anti-human CD3 antibody (BD Biosciences) and anti-human CD4 antibody (Ebioscience). The surface-stained FACS samples were permeabilized using a fixation/permeabilization kit (BD Biosciences), and subjected to intracellular cytokine FACS staining for anti-human IFN-γ antibody. Using the resulting FACS samples, cytokine secretion in T cells was analyzed using a FACScalibur (BD). To induce regulatory T cells, T cells were isolated according to the above-described method, and suspended in FBS (Gibco)-containing RPMI1640 (Gibco), and cultured with each test group for 7 days under the conditions of 37° C. and $CO_2$. After 7 days, T cells of each test group were collected and primarily FACS-stained with anti-human CD4 antibody and CD25 antibody. The surface-stained FACS samples were permeabilized using a fixation/permeabilization kit (Ebioscience). Each sample was subjected to intranuclear FACS staining for anti-human Foxp3 antibody, and then the induction (%) of regulatory cells in each sample was analyzed using a FACScalibur (BD).

Figure 6B:
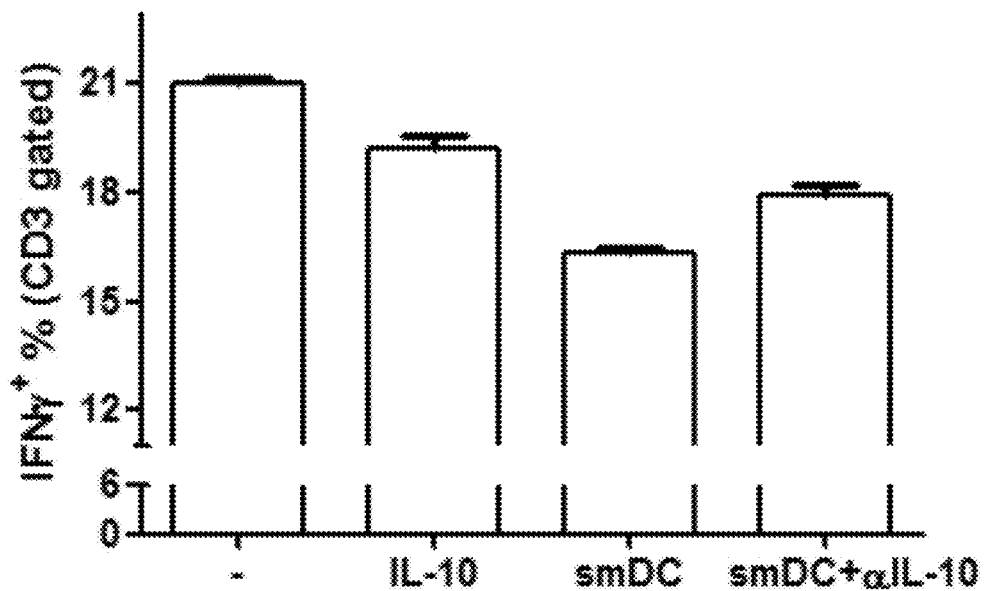
FIG. 6B shows experimental results indicating the IL-10-mediated inhibition of T-IFNγ secretion by semi-mature dendritic cells.
Figure 6C:
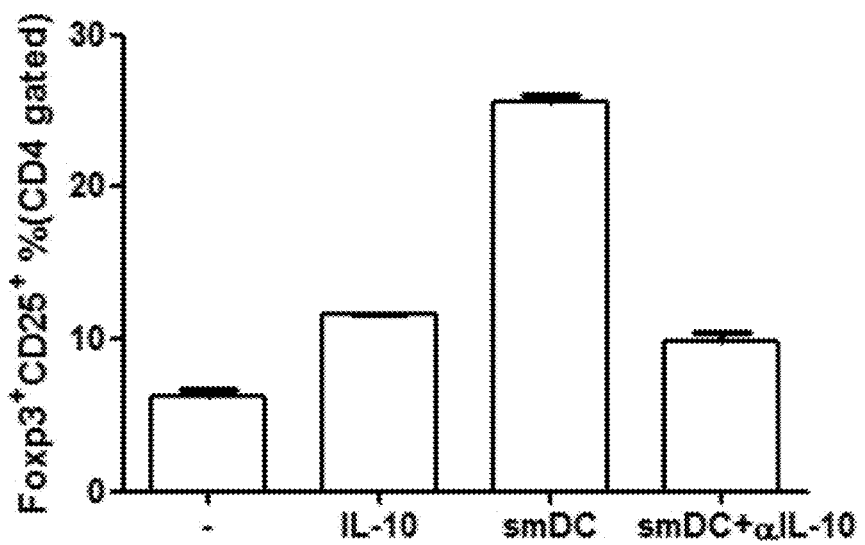
FIG. 6C shows experimental results indicating the IL-10-mediated induction of regulatory T cells by semi-mature dendritic cells.
Figure 7A:
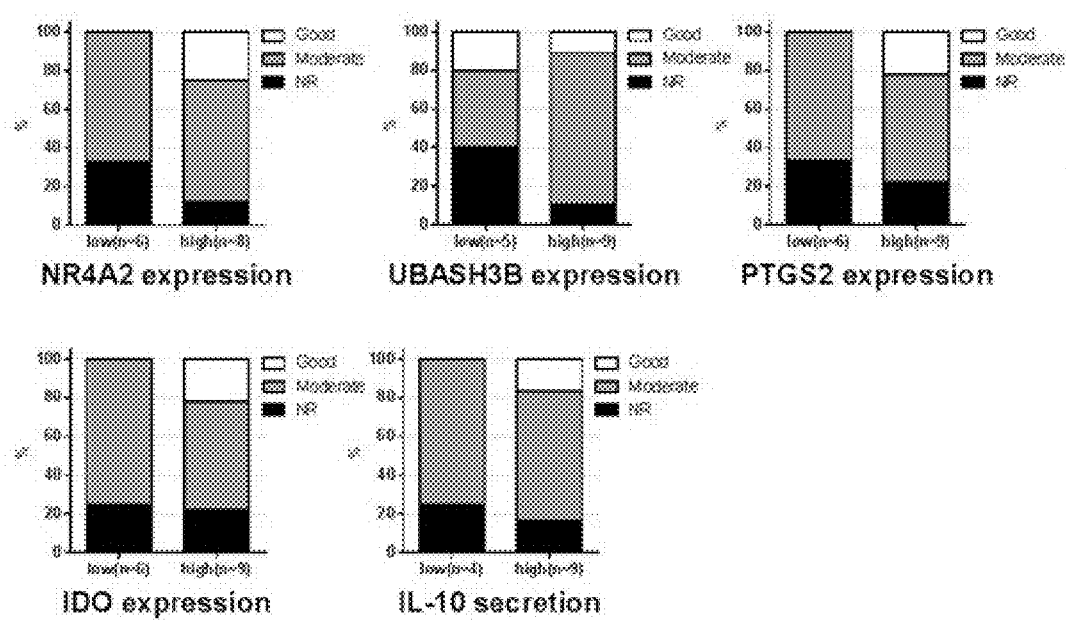
FIG. 7A shows experimental results indicating that gene expression in semi-mature dendritic cells, produced by a method of the present invention and having increased expression of a specific gene and increased secretion of IL-10, is effective for treatment of rheumatoid arthritis.
Figure 7B:
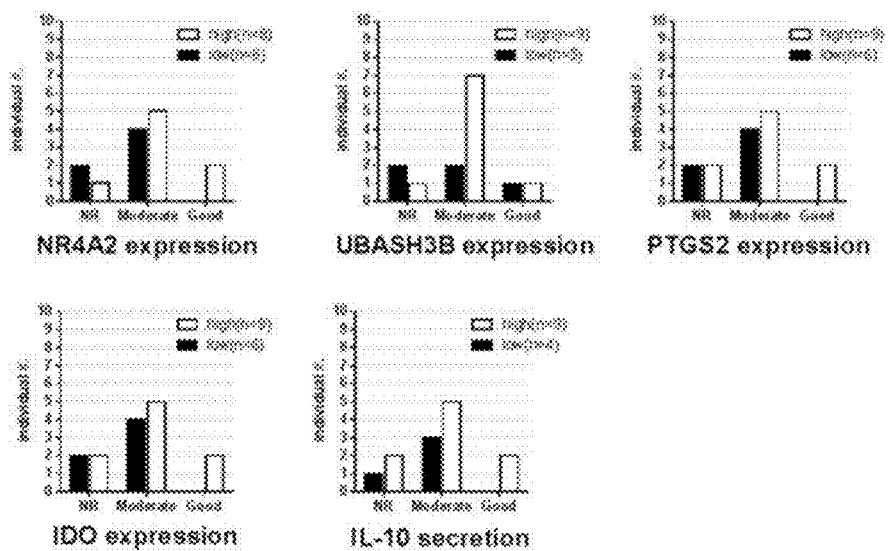
FIG. 7B experimental results indicating specific gene expression and IL-10 secretion and indicating that semi-mature dendritic cells, produced by a method of the present invention are effective for treatment of rheumatoid arthritis.

As a result, it could be seen that immune tolerance of T cells was achieved by IL-10 secreted from the semi-mature dendritic cells produced by the method of the present invention (FIGS. 6A, 6B, and 6C).

In addition, the semi-mature dendritic cells were administered to rheumatoid arthritis patients under the same conditions as described in Example 2, and then an assay was performed to monitor changes in the IFN-γ reactivities of autoreactive T cells against self-antigens (autoantigens) (immune response monitoring). Citrullinated filaggrin (JW CreaGene), PAD4 (JW CreaGene), RA33 (JW CreaGene) and vimentin (JW CreaGene) antigens (10 μg/mL) were used, and the spot in each well was analyzed using an ImmunoSPOT-ELISPOT reader (Cellular Technology).

Figure 9A:
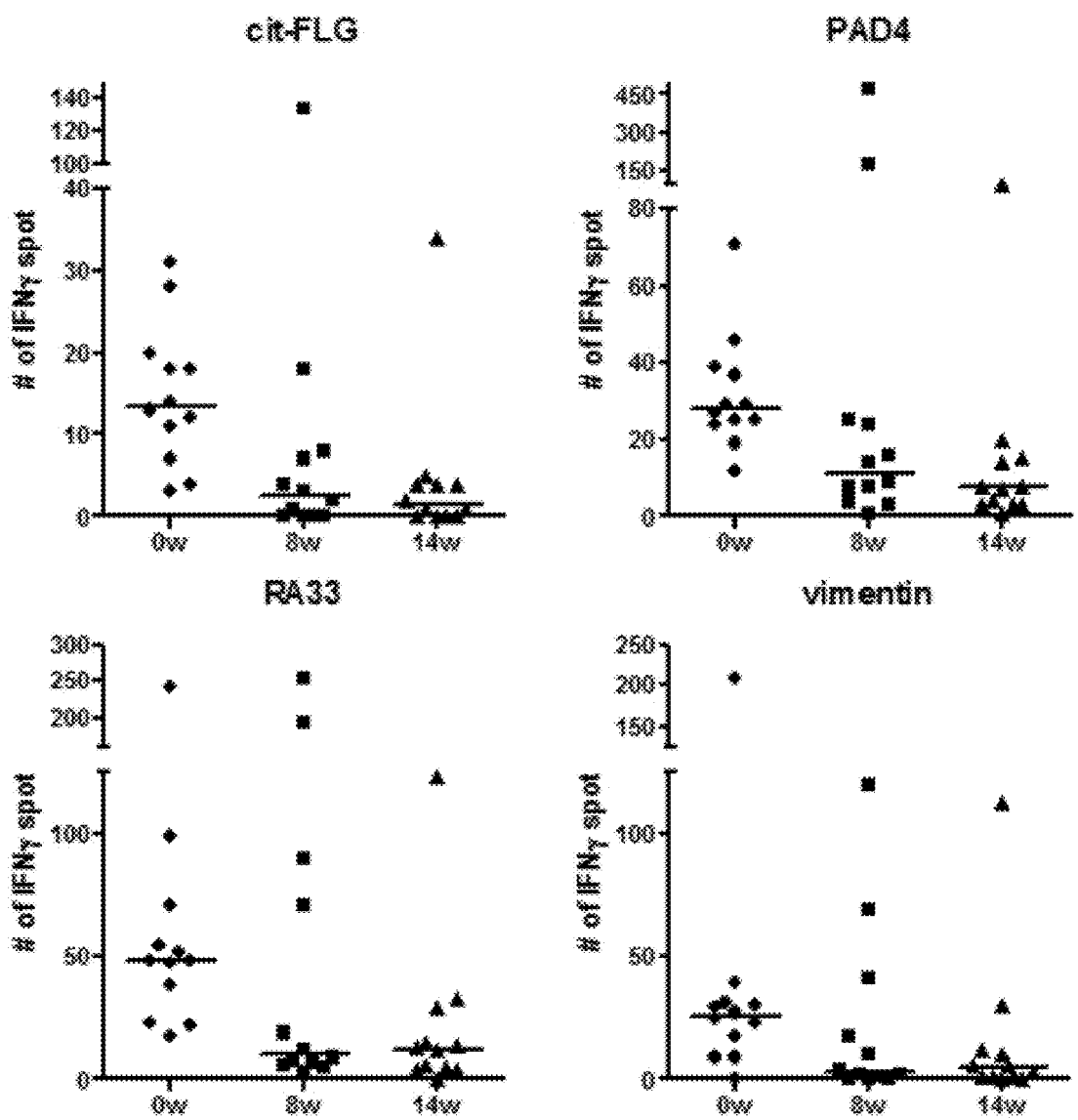
FIG. 9A shows the results of an ELISPOT assay performed to measure changes in T-cell responses (IFN-γ) of patients administered with semi-mature dendritic cells.
Figure 9B:
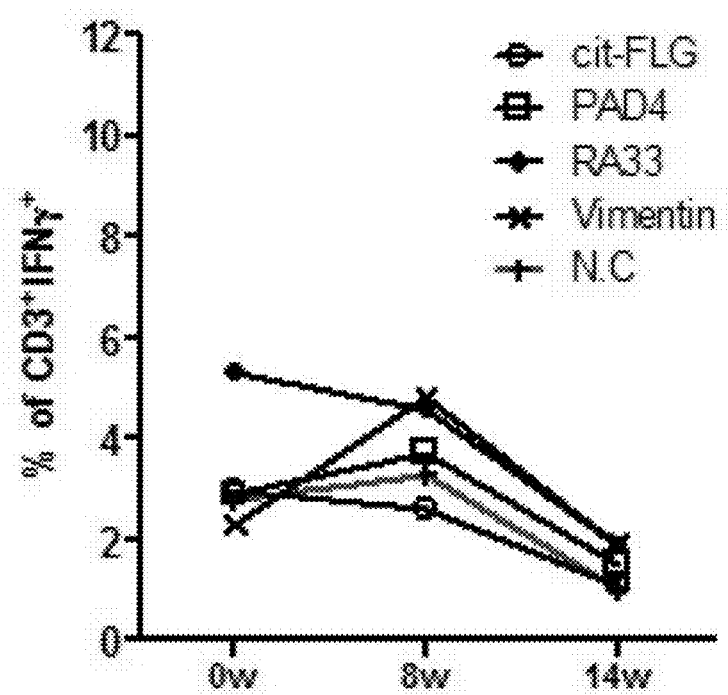
FIG. 9B shows the results of an IFN-γ intracellular staining assay performed to measure changes in T-cell responses (IFN-γ) of patients administered with semi-mature dendritic cells.

As a result, it could be seen that treatment with the semi-mature dendritic cells of the present invention inhibited the secretion of IFN-γ from T-cells in proportion to the treatment time to increase immune tolerance properties such as regulatory T-cell induction (FIGS. 9A and 9B).

Example 8: Administration of Semi-Mature Dendritic Cells and Blood Sampling for Immune Response Monitoring To immature dendritic cells extracted from the peripheral blood monocytes of rheumatoid arthritis patients, 7 μg/mL of each of the specific self-antigens (autoantigens: JW CreaGene) selected in Example 1 or 2, 10 ng/mL of TNFα (Peprotech) and 5 μg/mL of PGE2 (Sigma-Aldrich) were added, and the cells were stimulated by each of the antigens for 4 hours. After stimulation, the resulting semi-mature dendritic cells were mixed at a ratio of 1:1:1:1 and frozen at a concentration of $0.5 \times 10^7$ cells/0.5 mL or $1.5 \times 10^7$ cells/1.5 mL. Vials containing the frozen semi-mature dendritic cells were thawed, and the cells were injected subcutaneously into both femoral regions of 12 rheumatoid arthritis patients (divided into two groups (high-dose group and low-dose group), each consisting of 6 persons)) in an amount of $5 \times 10^6$ cells/0.5 mL or $1.5 \times 10^7$ cells/1.5 mL. Next, at 2, 4, 8 and 10 weeks, the semi-mature dendritic cells were administered in the same amount and manner as described above. Before administration and 8 and 14 weeks after administration, blood was sampled from the rheumatoid arthritis patients, and effectiveness evaluation and immune response monitoring were performed.

The results of the effectiveness evaluation indicated that the semi-mature dendritic cells of the present invention, in which the secretion of IL-10 was increased by expression of the NR4A2 and/or UBASH3B gene, were effective for treatment of rheumatoid arthritis (FIGS. 7A, 7B, and 8).

In addition, the results of the immune response monitoring indicated that autoantibodies against citrullinated filaggrin, PAD4 (peptidyl arginine deiminase 4), RA33 (heterogeneous nuclear ribonucleoprotein A2) and vimentin antigens significantly decreased, suggesting that the semi-mature dendritic cells of the present invention, sensitized with the specific antigens, are effective for treatment of rheumatoid arthritis (FIGS. 10 and 11).

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

INDUSTRIAL APPLICABILITY

As described above, according to the present invention, semi-mature dendritic cells may be produced by treating human immature dendritic cells with a selected specific self-antigen(autoantigen), a cytokine and PGE2. The produced semi-mature dendritic cells show an at least 2-fold increase in expression of NR4A2 or UBASH3B protein or a gene encoding the protein, compared to immature dendritic cells, and thus show increased secretion of IL-10, indicating that the semi-mature dendritic cells have increased immune tolerance properties.

When a cell therapeutic agent for prevention or treatment of autoimmune disease, which contains the semi-mature dendritic cells of the present invention, is administered to a patient showing responsiveness to the same self-antigen (autoantigen) as the autoantibody used in the production of the semi-mature dendritic cells, it exhibits excellent effects compared to conventional autoimmune disease therapeutics. Thus, the cell therapeutic agent enables cell therapy based on the characteristics of an individual patient.

The invention claimed is:

1. An in vitro method for generating semi-mature dendritic cells comprising a step of treating immature dendritic cells with one or more self-antigen(autoantigen) selected from the group consisting of citrullinated α-enolase, filaggrin, citrullinated filaggrin, PAD4 (peptidyl arginine deiminase 4), RA33 (heterogeneous nuclear ribonucleoprotein A2), citrullinated fibrinogen-α, citrullinated fibrinogen-β, vimentin peptides, and citrullinated vimentin peptides, a cytokine and prostaglandin E2 (PGE2); and confirming expression of NR4A2 and/or UBASH3B protein or mRNA encoding NR4A2 and/or UBASH3B protein is increased at least 2-fold compared to immature dendritic cells to select semi-mature dendritic cells.

2. The method of claim 1, further comprising selecting semi-mature dendritic cells in which expression of PTGS2 and/or IDO protein or mRNA encoding the protein is increased compared to immature dendritic cells.

3. The method of claim 1, wherein the immature dendritic cells are treated with the self-antigen(autoantigen), the cytokine, and PGE2 for 3-10 hours.

4. The method of claim 1, wherein the cytokine is TNF-α (tumor necrosis factor-alpha).

5. The method of claim 1, wherein the concentration of PEG2 used to treat the cells is 0.05-5 μg/mL.

* * * * *

UNITED STATES PATENT AND TRADEMARK OFFICE
CERTIFICATE OF CORRECTION

PATENT NO. : 10,350,279 B2
APPLICATION NO. : 15/320010
DATED : July 16, 2019
INVENTOR(S) : Bae et al.

Page 1 of 1

It is certified that error appears in the above-identified patent and that said Letters Patent is hereby corrected as shown below:

In the Specification

Column 12, Line 60: "persons×1.5>" should be -- persons × 1.5> --.

Column 13, Line 40: "persons×1.5>" should be -- persons × 1.5> --.

Signed and Sealed this
Third Day of September, 2019

Andrei Iancu
*Director of the United States Patent and Trademark Office*

SEQUENCE LISTING

```
<160> NUMBER OF SEQ ID NOS: 14

<210> SEQ ID NO 1
<211> LENGTH: 24
<212> TYPE: DNA
<213> ORGANISM: Artificial Sequence
<220> FEATURE:
<223> OTHER INFORMATION: Forward Primer NR4A2

<400> SEQUENCE: 1
gccatgcttg gttgttgcag ttca                                             24

<210> SEQ ID NO 2
<211> LENGTH: 24
<212> TYPE: DNA
<213> ORGANISM: Artificial Sequence
<220> FEATURE:
<223> OTHER INFORMATION: Reverse Primer NR4A2

<400> SEQUENCE: 2
tcatgccacc cacgcaacat ttag                                             24

<210> SEQ ID NO 3
<211> LENGTH: 24
<212> TYPE: DNA
<213> ORGANISM: Artificial Sequence
<220> FEATURE:
<223> OTHER INFORMATION: Forward Primer UBASH3B
```

```
<400> SEQUENCE: 3
aagcaagact agtgggtgaa gcct                                          24

<210> SEQ ID NO 4
<211> LENGTH: 24
<212> TYPE: DNA
<213> ORGANISM: Artificial Sequence
<220> FEATURE:
<223> OTHER INFORMATION: Reverse Primer UBASH3B

<400> SEQUENCE: 4
aaataagccg ggctctacac ggat                                          24

<210> SEQ ID NO 5
<211> LENGTH: 24
<212> TYPE: DNA
<213> ORGANISM: Artificial Sequence
<220> FEATURE:
<223> OTHER INFORMATION: Forward Primer PTGS2

<400> SEQUENCE: 5
gcctatgtgc tagcccacaa agaa                                          24

<210> SEQ ID NO 6
<211> LENGTH: 24
<212> TYPE: DNA
<213> ORGANISM: Artificial Sequence
<220> FEATURE:
<223> OTHER INFORMATION: Reverse Primer PTGS2

<400> SEQUENCE: 6
acgaagcatc cacagatccc tcaa                                          24

<210> SEQ ID NO 7
<211> LENGTH: 20
<212> TYPE: DNA
<213> ORGANISM: Artificial Sequence
<220> FEATURE:
<223> OTHER INFORMATION: Forward Primer IDO

<400> SEQUENCE: 7
gatgaagaag tggggtttgc                                               20

<210> SEQ ID NO 8
<211> LENGTH: 20
<212> TYPE: DNA
<213> ORGANISM: Artificial Sequence
<220> FEATURE:
<223> OTHER INFORMATION: Reverse Primer IDO

<400> SEQUENCE: 8
cgctgtgact tgtggtctgt                                               20

<210> SEQ ID NO 9
<211> LENGTH: 24
<212> TYPE: DNA
<213> ORGANISM: Artificial Sequence
<220> FEATURE:
<223> OTHER INFORMATION: Forward Primer beta-actin

<400> SEQUENCE: 9
ggcacccagc acaatgaaga tcaa                                          24

<210> SEQ ID NO 10
<211> LENGTH: 24
```

<212> TYPE: DNA
<213> ORGANISM: Artificial Sequence
<220> FEATURE:
<223> OTHER INFORMATION: Reverse Primer beta-actin

<400> SEQUENCE: 10
actcgtcata ctcctgcttg ctga                                           24

<210> SEQ ID NO 11
<211> LENGTH: 3546
<212> TYPE: DNA
<213> ORGANISM: Homo sapiens

<400> SEQUENCE: 11
gctgacgcgc gctgacgcgc ggagacttta ggtgcatgtt ggcagcggca gcgcaagcca      60
cataaacaaa ggcacattgg cggccagggc cagtccgccc ggcggctcgc gcacggctcc     120
gcggtccctt ttgcctgtcc agccggccgc ctgtccctgc tccctccctc cgtgaggtgt     180
ccgggttccc ttcgcccagc tctcccaccc ctacccgacc ccggcgcccg ggctcccaga     240
gggaactgca cttcggcaga gttgaatgaa tgaagagaga cgcggagaac tcctaaggag     300
gagattggac aggctggact ccccattgct tttctaaaaa tcttggaaac tttgtccttc     360
attgaattac gacactgtcc acctttaatt tcctcgaaaa cgcctgtaac tcggctgaag     420
ccatgccttg tgttcaggcg cagtatgggt cctcgcctca aggagccagc ccgcttctc      480 agagctacag ttaccactct tcgggagaat acagctccga tttcttaact ccagagtttg     540
tcaagtttag catggacctc accaacactg aaatcactgc caccacttct ctccccagct     600
tcagtacctt tatggacaac tacagcacag gctacgacgt caagccacct tgcttgtacc     660 aaatgccccct gtccggacag cagtcctcca ttaaggtaga agacattcag atgcacaact     720
accagcaaca cagccacctg cccccccagt ctgaggagat gatgccgcac tccgggtcgg     780
tttactacaa gccctcctcg cccccgacgc ccaccacccc gggcttccag gtgcagcaca     840
gccccatgtg ggacgacccg ggatctctcc acaacttcca ccagaactac gtggccacta     900
cgcacatgat cgagcagagg aaaacgccag tctcccgcct ctccctcttc tcctttaagc     960
aatcgccccc tggcacccct gtgtctagtt gccagatgcg cttcgacggg cccctgcacg    1020
tccccatgaa cccggagccc gccggcagcc accacgtggt ggacgggcag accttcgctg    1080
tgcccaaccc cattcgcaag cccgcgtcca tgggcttccc gggcctgcag atcggccacg    1140
cgtctcagct gctcgacacg caggtgccct caccgccgtc gcggggctcc ccctccaacg    1200
aggggctgtg cgctgtgtgt ggggacaacg cggcctgcca acactacggc gtgcgcacct    1260
gtgagggctg caaaggcttc tttaagcgca cagtgcaaaa aaatgcaaaa tacgtgtgtt    1320
tagcaaataa aaactgccca gtggacaagc gtcgccggaa tcgctgtcag tactgccgat    1380
ttcagaagtg cctggctgtt gggatggtca agaagtggt tcgcacagac agtttaaaag    1440
gccggagagg tcgtttgccc tcgaaaccga agagcccaca ggagccctct cccccttcgc    1500
ccccggtgag tctgatcagt gccctcgtca gggcccatgt cgactccaac ccggctatga    1560
ccagcctgga ctattccagg ttccaggcga accctgacta tcaaatgagt ggagatgaca    1620
cccagcatat ccagcaattc tatgatctcc tgactggctc catggagatc atccggggct    1680
gggcagagaa gatccctggc ttcgcagacc tgcccaaagc cgaccagac ctgcttttg     1740 aatcagcttt cttagaactg tttgtccttc gattagcata caggtccaac ccagtggagg    1800
gtaaactcat cttttgcaat ggggtggtct tgcacaggtt gcaatgcgtt cgtggctttg    1860

```
gggaatggat tgattccatt gttgaattct cctccaactt gcagaatatg aacatcgaca    1920
tttctgcctt ctcctgcatt gctgccctgg ctatggtcac agagagacac gggctcaagg    1980
aacccaagag agtggaagaa ctgcaaaaca agattgtaaa ttgtctcaaa gaccacgtga    2040
cttccaacaa tggggggttg aaccgcccca attatttgtc caaactgttg gggaagctcc    2100
cagaacttcg tacccttgc acacaggggc tacagcgcat tttctacctg aaattggaag    2160
acttggtgcc accgccagca ataattgaca aactttcct ggacacttta cctttctaag    2220
acctcctccc aagcacttca aggaactggg aatgataatg aaactgtca agaggggca    2280 agtcacatgg gcagagatag ccgtgtgagc agtctcagct caagctgccc cccatttctg    2340
taaccctcct agccccttg atccctaaag aaaacaaaca aacaaacaaa aactgttgct    2400
atttcctaac ctgcaggcag aacctgaaag gcattttgg ctccggggca tcctggattt    2460
agaacatgga ctacacacaa tacagtggta taaactttt attctcagtt taaaaatcag    2520
tttgttgttc agaagaaaga ttgctataat gtataatggg aaatgtttgg ccatgcttgg    2580
ttgttgcagt tcagacaaat gtaacacaca cacacataca cacacacaca cacacagag    2640 gacacatctt aaggggaccc acaagtattg ccctttaaca agacttcaaa gttttctgct    2700
gtaaagaaag ctgtaatata tagtaaaact aaatgttgcg tgggtggcat gagttgaaga    2760
aggcaaaggc ttgtaaattt acccaatgca gttttggcttt ttaaattatt ttgtgcctat    2820
ttatgaataa atattacaaa ttctaaaaga taagtgtgtt tgcaaaaaa aagaaaataa    2880 atacataaaa aagggacaag catgttgatt ctaggttgaa aatgttatag gcacttgcta    2940
cttcagtaat gtctatattta ataaaatagt atttcagaca ctatgtagtc tgttagattt    3000
tataaagatt ggtagttatc tgagcttaaa cattttctca attgtaaat aggtgggcac    3060 aagtattaca catcagaaaa tcctgacaaa agggacacat agtgttttgta acaccgtcca    3120 acattccttg tttgtaagtg ttgtatgtac cgttgatgtt gataaaaaga agtttatat    3180 cttgattatt ttgttgtcta aagctaaaca aaacttgcat gcagcagctt ttgactgttt    3240
ccagagtgct tataatatac ataactccct ggaaataact gagcactttg aatttttt    3300 atgtctaaaa ttgtcagtta atttattatt ttgtttgagt aagaatttta atattgccat    3360
attctgtagt attttctttt gtatatttct agtatggcac atgatatgag tcactgcctt    3420
tttttctatg gtgtatgaca gttagagatg ctgatttttt ttctgataaa ttctttctttt    3480 gagaaagaca atttttaatgt ttacaacaat aaaccatgta aatgaacaga aaaaaaaa    3540 aaaaaa                                                                 3546

<210> SEQ ID NO 12
<211> LENGTH: 6917
<212> TYPE: DNA
<213> ORGANISM: Homo sapiens

<400> SEQUENCE: 12
cttttccttt ttgatccatt caaaaattac tcattgcaaa ttcccggact gctaggcgag      60
gagagggaag ggggcggagg agacagggct actgcaggcg cagagctggg ggcagccggg     120
ggcccgagtg gctgaggctg gtccgcagc ggccgcttgc cggcgttctg gctcctgtgg     180
cctcaccagg aagcgtcaga gtcccgacac tggggaagct cggagcgccg cctccgctgc     240
cgccgcctcc tgcctggctc tgggtccccg agccccctcc cctggcccag cccgactccc     300
tcctccttcc cgaaccatcc ggctcgggct ccttccctgg cgatggctgg ccgctgagcc     360
atggctcagt acggccaccc cagtccgctc ggcatggctg cgagagagga gctgtacagc     420
```

```
aaagtcaccc cccggaggaa ccgccaacag cgccccggca ccatcaagca tggatcggcg     480
ctggacgtgc tcctctccat gggggttcccc agagcccgcg cacaaaaagc cttggcatcc    540
acgggaggaa gaagtgttca ggcagcatgt gactggttat tctcccatgt cggtgacccc    600
ttcctggatg acccccctgcc ccgggagtac gtcctctacc tccgtcccac cggcccctta   660
gcacagaagc tttccgactt tggcagcag tcgaagcaga tctgcgggaa gaacaaggca     720
cacaacatct tccccccacat cacactctgc cagttcttta tgtgcgagga cagcaaggtg   780
gatgccctgg ggaagccct gcagaccacg gtcagtcgct ggaaatgtaa gttctcggcc     840
ccgctgcccc tggagctcta tacgtcgtcc aacttcatcg gcctctttgt aaaggaagac    900
agtgcggagg tcctcaagaa gtttgctgct gactttgctg cagaggctgc atccaaaacc    960
gaagtgcatg tggaacctca taagaagcag ctacatgtga ccctggctta ccacttccaa   1020
gccagccacc tacccacccct agagaaactg gcccagaaca ttgacgtcaa gctagggtgt  1080
gactgggtgg ctaccatatt ttctcgggat atccgatttg ctaaccatga gacattacag   1140
gtcatctacc cctataccccc acaaaatgac gatgagctgg agctggtccc cggggacttc  1200
atcttcatgt ctccaatgga gcagaccagc accagcgagg gttggatcta tggcacgtcc   1260
ttaaccaccg gctgctctgg actcctgcct gagaattaca ttaccaaggc tgatgaatgc   1320
agcacctgga tatttcatgg ttcttattca atcttaaata tcgtcatcc caactctctc    1380 acgtttgggg atggagtatt ggagaggcgg ccttatgagg accaggggct cggggagacg   1440 actcctcttta ctatcatctg ccagcccatg cagccgctga gggtcaacag ccagcccggc  1500
ccccagaagc gatgccttttt tgtgtgtcgg catggtgaga ggatggatgt tgtgtttggg  1560
aagtactggc tgtcccagtg cttcgatgcc aaaggccgct acatacgcac caacctgaac   1620
atgcctcata gtttacctca gcggagtggt ggtttccgag attacgagaa agatgctccc   1680
atcactgtgt ttggatgcat gcaagcaaga ctagtgggtg aagccttatt agagagcaat   1740
accattatcg atcatgtcta ttgctccccg tcccttcgct gcgttcagac tgcacacaat   1800
atcttgaaag gttacaaca agaaaatcac ttgaagatcc gtgtagagcc cggcttattt    1860
gagtggacaa aatgggttgc tgggagcaca ttacctgcat ggatacctcc atcagagtta   1920
gctgcagcca acctgagtgt tgatacaacc tacagacctc acattccaat cagcaaatta   1980
gttgtttcag aatcctatga tacttatatc agtagaagtt tccaagtaac aaaagaaata   2040
ataagtgaat gtaaaagtaa aggaaataac atcctgattg tggcccacgc atcttccctt   2100
gaagcgtgta cctgccaact tcagggcctg tcacctcaga actccaagga cttcgtacaa   2160
atggtccgaa agatcccata tctgggattt tgttcctgtg aagaattagg agaaactgga   2220
atatggcagc tgacagatcc accaatcctt cctcttaccc atggaccaac tgggggcttc   2280
aactggagag agaccttgct tcaagaataa accacaccag tgaacaagaa ggaaaggcct   2340
tttggagtgt gtctttctgt gtgtttaaaa acagtgggaa aatccacacc acactctaag   2400
tggacagctc agaataattt agcatatttc cttttcacact taaagttctt aagatgagac   2460
tgtgtaaatg agagaaagac ttgattcaga ggaaaaaaat gtgttctctc tggactcttg   2520
cctagctcac aaggctttgg agaattgtct tcctaaatcg gggcacctgc tacagaagag   2580
aatgtttcgt tccctctggg tatgcacagc taaggggcct catttctccc agagggagct   2640
gctgccccgc tctaagggggt gcaagaggaa ggagtgtgcc cagaccagct gggggagcat  2700
tgaaaggaca gcttggggat ggaattttttt tttttttatc tccattttcc agttaggtag  2760
```

```
agccaagctg aggaatcctt ttaagattat tagaaaacat gccctgaaga gagttgttct   2820
taggttacac atgaaatcct accgtcacta gcccccatac accagtgttg ctggctgaag   2880
atacccgctt aaggatgcta acatttaccc tggtactgcc acattttctc tagagcagct   2940
ggccttctt gctacagccc tatccccct ccttgcttct gtgaaatggg gagacaaagc   3000
acttttgctc tccaaagcac ttttggatac tcaggaggaa agataagata catgtttgaa   3060
gtattcaatc ataggagcaa agaacttgca aaatatgaag tgacttggaa ttaaccatgt   3120
tgtagcctaa cgtgctactg catttctaaa tcatcaatat ttgcttgtct ttgcccctag   3180
actctagact atgttaacta gttaaggatg ttacattttg aaaggatgta tgttagatat   3240
attatttgca gcaagaagtt cattctgtgc aatatggaca tgtttgcaaa ccataccaag   3300
ggtcaggttg ttgtacactt acagtacgtg tcaaccataa tggaacatcc acaaatgcat   3360
caattatacc agggatgtat agtaagtcag ggaactaata taaatgatga cagtcatggc   3420
tgcactgcta cttgtgctgt cgttttgttt gttttctat gataatttaa aatacatagg   3480
tagggctact gaggaaattt ggagagccac attctgtggt ttctcattat acttacttcc   3540
tgcatttaga gggagtttat ttaaaagaaa taaatgacaa tcaaaccaaa tcatcagtta   3600
tcaatgtctg tttaattgtg tgactatctg actgttgatg ccacagatg atggtctcct   3660
atggtatagt tcactctgta gaagatgtat gcaaagtgaa atgccagccc tttaaagaga   3720
cattagttag tgtaaaatgg atctttacat gttgcagtaa cattgactat gtttcaaaac   3780
tcagatgcat aaaacgtaag gtatataaaa atacatctat gcttgcgttt gaaactacaa   3840
cttgataacc cctagaaaga agaggacatg aaaggatgct ggctatatat gttaatgagc   3900
aaaaggatta tagttgtttt gttttgtttt tagagacagg gtctcactat aatgcttaga   3960
ctggtcttga actcctgggc tcaagcgatc ctcctgcccc tgtctcccaa agtgctagga   4020
ttacaggtgt gagccaccac acctggccca tagttgtatt ttttttaggt cacttagaaa   4080
aatatgtcat gtatttaca ttttgagaaa caaatcaatc atggtttctt ctagcgttgc   4140
gcaaacactg acccagcttc tgggtatgga aataaccctg tgatgatgtg ttaatataaa   4200
atgttgggag ggaatattcc caataaaggt cttaagagaa aagtcacatt acaagtaatg   4260
taatggctct accattcatt cttctggtat ttgtaatgaa gtgaatccac tgtttaatca   4320
gatccataat ctttaacaga ttcaccacaa attttcatgg gcgttgagtg ctcagaataa   4380
tgcttgaaca ccctcacctttg aaactgtagc agtgtgttct gggcagtatc tgtaatgtat   4440
gaaatagagt ctggaatagg ttatccactc catcttctag gttatcttag ttgtatgacg   4500
aactgataaa tctgtctgac tgggctacaa tccattgttc ttagtccaat atggacactg   4560
ccttaggcaa tggtctatat aagcaaaagg agatagagat ctgaaataat tttccgaata   4620
attcaggtgg aaaacaagaa agattgtatt tctctgcttt catttcaatt tcattatttc   4680
aaattgcttg tcaaaatggc ccaaaagatc tgaattcaca ttaagttccc cttgcacact   4740
tacctattta aaaaactaaa cttgcactgc aactgagaaa ttatttgtaa atcatgtggc   4800
atctatgtat aataaagaa agagacaact atattactca atttcatata catccaaaaa   4860
gtataggcta atatatataa cctgaagttg cagctggttc tttttgatct gaagctgatg   4920
cttattaaaa caaatgatgt atggggagag gagaaggaag ggcaaggaag gaattgacag   4980
ataagaagca aatggtttct tgtacagagg aattttgttt taatgtagaa agttatttga   5040
aataaactag gtgaaatgaa attaactaaa ggttttaatc tgggattgaa agcctgaaag   5100
catttcctgc ttctacaagt gtgccacatc aatccggtaa tgccccagtg ttattcacag   5160
```

| | |
|---|---|
| acagaactتt gtttcctgtg attttaaaat accgcgtctg ttcctccatg gaccagagta | 5220 |
| attggcacat tttaatgcat aagctggggg tttcattttc ccaggctctc ttcaccatca | 5280 |
| ctgcattggt agctaggagc ttattgcttc accccagtat ggagttcaga ttacagtgtt | 5340 |
| ttccattaca tttagattca tagaatctga atggctgatt aaatggccat ctgatggctg | 5400 |
| aaagaggggc gtattttca ctctgtagtg aaaggcttgg aggagtttct acttttatt | 5460 |
| ttaattatac tttaaccaaa gaattatttt aaagtaacct tatatttaaa agatgatttt | 5520 |
| gcaaaaaata aaaataaaa aatatgcctt ctggagtgat gtctgtttgg taaatcattg | 5580 |
| ttgataattt ccttgttagt ggtatttgga atgcatatag attgtcttgt cattgtgctt | 5640 |
| aacattacca taagtgtgtc ttttccactc aactagctgt attcgtatta aaatgaagtc | 5700 |
| tcttatttca attacctagt gttgttggga actaattgaa cagctacagt aaaagaagtt | 5760 |
| cctatctcat tgcctttgtg gaaaggcttc cctatgtggt aaaagaaagg cattcctccg | 5820 |
| taacctaggc actctgcaag tccagtgttt aatttcaaag cagtgatgaa ttgctctttt | 5880 |
| gaaattactc taagtaatcc atgtgttaga atacagatga acctccgttt gatttcacag | 5940 |
| ccttcagcac aggcaactgt tactgagtct gcacgaactt agataatgag gtgcagggtt | 6000 |
| atttgcattt aaattgcaat ccagcacacg tgtgagaaag aagaggcact agtctaaaag | 6060 |
| gctgcattgc ggggagagat gagacaggca gaggagggtg gggtaaagag cgatttaaca | 6120 |
| tctatttagg ttaatgttca ctttacaaag gtgatggggg atattttgtt aggtgatagc | 6180 |
| agaagctttt cattttttaaa catagaatta aaattggatt tgcttctctt taatacttca | 6240 |
| acatattgaa tttccctagg aaagtgacta gctataatga aaattcaagc gaaaagggaa | 6300 |
| aaagattgta aatgcagatg aaataacttc attttttaagt acaaataata gtaggattgg | 6360 |
| tgtatgtagg tttaaaatta tagtgatgac tagtcgaact taatatacaa tcagttcttg | 6420 |
| caaatacttt acacttagct gccattacac aacaaattgg aattttccag ctgttcaact | 6480 |
| atcatggact ctgtacagga tagatgtgta taatggaaaa tatgtactgc ttctttcttt | 6540 |
| gattgccact caagatggaa acaccatgcc aaggcatttt ggttatacac agatcattct | 6600 |
| aaacctgtta ttttggagag gtgtattggt ttcttttctca tttataaggc tattgtatt | 6660 |
| ttttttgtat gtgattcagg tgtatttatt tgaagactat ttgtagttat aggaaaaacca | 6720 |
| cacctacctg tattgccaaa ttctttgtaa actctccgtg gcacttgtgc tttcctggct | 6780 |
| gagagctctc ccctgttgat acagctatgg caccattgta attacagatg cacctttcag | 6840 |
| gagcatctcc attaaatggt tcatagatga tttaataaaa agaaacttct cagttgatcc | 6900 |
| agaaaaaaaa aaaaaaa | 6917 |

<210> SEQ ID NO 13
<211> LENGTH: 4507
<212> TYPE: DNA
<213> ORGANISM: Homo sapiens

<400> SEQUENCE: 13

| | |
|---|---|
| gaccaattgt catacgactt gcagtgagcg tcaggagcac gtccaggaac tcctcagcag | 60 |
| cgcctccttc agctccacag ccagacgccc tcagacagca aagcctaccc ccgcgccgcg | 120 |
| ccctgcccgc cgctgcgatg ctcgcccgcg ccctgctgct gtgcgcggtc ctggcgctca | 180 |
| gccatacagc aaaatccttg ctgttcccac catgtcaaaa ccgaggtgta tgtatgagtg | 240 |
| tgggatttga ccagtataag tgcgattgta cccggacagg attctatgga gaaaactgct | 300 |

```
caacaccgga attttttgaca agaataaaat tatttctgaa acccactcca aacacagtgc    360
actacatact tacccacttc aagggatttt ggaacgttgt gaataacatt cccttccttc    420
gaaatgcaat tatgagttat gtgttgacat ccagatcaca tttgattgac agtccaccaa    480
cttacaatgc tgactatggc tacaaaagct gggaagcctt ctctaacctc tcctattata    540
ctagagccct tcctcctgtg cctgatgatt gcccgactcc cttgggtgtc aaaggtaaaa    600
agcagcttcc tgattcaaat gagattgtgg aaaaattgct tctaagaaga aagttcatcc    660
ctgatcccca gggctcaaac atgatgtttg cattctttgc ccagcacttc acgcatcagt    720
ttttcaagac agatcataag cgagggccag cttttcaccaa cgggctgggc catggggtgg    780
acttaaatca tatttacggt gaaactctgg ctagacagcg taaactgcgc cttttcaagg    840
atggaaaaat gaaatatcag ataattgatg gagagatgta tcctcccaca gtcaaagata    900
ctcaggcaga gatgatctac cctcctcaag tccctgagca tctacggttt gctgtggggc    960
aggaggtctt tggtctggtg cctggtctga tgatgtatgc cacaatctgg ctgcgggaac   1020
acaacagagt atgcgatgtg cttaaacagg agcatcctga tggggtgat gagcagttgt   1080 tccagacaag caggctaata ctgataggag agactattaa gattgtgatt gaagattatg   1140
tgcaacactt gagtggctat cacttcaaac tgaaatttga cccagaacta cttttcaaca   1200
aacaattcca gtaccaaaat cgtattgctg ctgaatttaa caccctctat cactggcatc   1260
cccttctgcc tgacaccttt caaattcatg accagaaata caactatcaa cagtttatct   1320
acaacaactc tatattgctg aacatggaa ttacccagtt tgttgaatca ttcaccaggc   1380
aaattgctgg cagggttgct ggtggtagga atgttccacc cgcagtacag aaagtatcac   1440
aggcttccat tgaccagagc aggcagatga ataccagtc ttttaatgag taccgcaaac   1500
gctttatgct gaagccctat gaatcatttg aagaacttac aggagaaaag gaaatgtctg   1560
cagagttgga agcactctat ggtgacatcg atgctgtgga gctgtatcct gcccttctgg   1620
tagaaaagcc tcggccagat gccatctttg gtgaaaccat ggtagaagtt ggagcaccat   1680
tctccttgaa aggacttatg ggtaatgtta tatgttctcc tgcctactgg aagccaagca   1740
cttttggtgg agaagtgggt tttcaaatca tcaacactgc ctcaattcag tctctcatct   1800
gcaataacgt gaagggctgt ccctttactt cattcagtgt tccagatcca gagctcatta   1860
aaacagtcac catcaatgca agttcttccc gctccggact agatgatatc aatcccacag   1920
tactactaaa agaacgttcg actgaactgt agaagtctaa tgatcatatt tatttattta   1980
tatgaaccat gtctattaat ttaattattt aataatatt atattaaact ccttatgtta   2040
cttaacatct tctgtaacag aagtcagtac tcctgttgcg gagaaaggag tcatacttgt   2100
gaagactttt atgtcactac tctaaagatt ttgctgttgc tgttaagttt ggaaaacagt   2160
ttttattctg ttttataaac cagagagaaa tgagttttga cgtcttttta cttgaatttc   2220
aacttatatt ataagaacga aagtaaagat gtttgaatac ttaaacactg tcacaagatg   2280
gcaaaatgct gaaagttttt acactgtcga tgtttccaat gcatcttcca tgatgcatta   2340
gaagtaacta atgtttgaaa ttttaaagta cttttggtta tttttctgtc atcaaacaaa   2400
aacaggtatc agtgcattat taaatgaata tttaaattag acattaccag taatttcatg   2460
tctacttttt aaaatcagca atgaaacaat aatttgaaat ttctaaattc atagggtaga   2520
atcacctgta aaagcttgtt tgatttctta aagttattaa acttgtacat ataccaaaaa   2580
gaagctgtct tggatttaaa tctgtaaaat cagtagaaat tttactacaa ttgcttgtta   2640
aaatatttta taagtgatgt tccttttttca ccaagagtat aaaccttttt agtgtgactg   2700
```

```
ttaaaacttc cttttaaatc aaaatgccaa atttattaag gtggtggagc cactgcagtg    2760
ttatcttaaa ataagaatat tttgttgaga tattccagaa tttgtttata tggctggtaa    2820
catgtaaaat ctatatcagc aaagggtct accttttaaaa taagcaataa caaagaagaa    2880
aaccaaatta ttgttcaaat ttaggtttaa acttttgaag caaacttttt tttatccttg    2940
tgcactgcag gcctggtact cagattttgc tatgaggtta atgaagtacc aagctgtgct    3000
tgaataatga tatgttttct cagattttct gttgtacagt ttaatttagc agtccatatc    3060
acattgcaaa agtagcaatg acctcataaa atacctcttc aaaatgctta aattcatttc    3120
acacattaat tttatctcag tcttgaagcc aattcagtag gtgcattgga atcaagcctg    3180
gctacctgca tgctgttcct tttcttttct tcttttagcc attttgctaa gagacacagt    3240
cttctcatca cttcgtttct cctatttgt tttactagtt ttaagatcag agttcacttt    3300
ctttggactc tgcctatatt ttcttacctg aacttttgca agttttcagg taaacctcag    3360
ctcaggactg ctatttagct cctcttaaga agattaaaag agaaaaaaaa aggcccttt    3420 aaaaatagta tacacttatt ttaagtgaaa agcagagaat tttatttata gctaatttta    3480
gctatctgta accaagatgg atgcaaagag gctagtgcct cagagagaac tgtacggggt    3540
ttgtgactgg aaaaagttac gttcccattc taattaatgc cctttcttat ttaaaaacaa    3600
aaccaaatga tatctaagta gttctcagca ataataataa tgacgataat acttcttttc    3660
cacatctcat tgtcactgac atttaatggt actgtatatt acttaattta ttgaagatta    3720
ttatttatgt cttattagga cactatggtt ataaactgtg tttaagccta caatcattga    3780 ttttttttg ttatgtcaca atcagtatat tttctttggg gttacctctc tgaatattat    3840
gtaaacaatc caaagaaatg attgtattaa gatttgtgaa taaattttta gaaatctgat    3900
tggcatattg agatatttaa ggttgaatgt ttgtccttag gataggccta tgtgctagcc    3960
cacaaagaat attgtctcat tagcctgaat gtgccataag actgaccttt taaaatgttt    4020
tgagggatct gtggatgctt cgttaatttg ttcagccaca atttattgag aaaatattct    4080
gtgtcaagca ctgtgggttt taatattttt aaatcaaacg ctgattacag ataatagtat    4140
ttatataaat aattgaaaaa aatttttcttt tgggaagagg gagaaaatga aataaatatc    4200
attaaagata actcaggaga atcttctttta caattttacg tttagaatgt ttaaggttaa    4260
gaaagaaata gtcaatatgc ttgtataaaa cactgttcac tgtttttttt aaaaaaaaaa    4320
cttgatttgt tattaacatt gatctgctga caaaacctgg gaatttgggt tgtgtatgcg    4380
aatgtttcag tgcctcagac aaatgtgtat ttaacttatg taaaagataa gtctggaaat    4440
aaatgtctgt ttatttttgt actatttaaa aattgacaga tcttttctga agaaaaaaaa    4500
aaaaaaa                                                              4507

<210> SEQ ID NO 14
<211> LENGTH: 1572
<212> TYPE: DNA
<213> ORGANISM: Homo sapiens

<400> SEQUENCE: 14
aatttctcac tgcccctgtg ataaactgtg gtcactggct gtggcagcaa ctattataag      60
atgctctgaa aactcttcag acactgaggg gcaccagagg agcagactac aagaatggca     120
cacgctatgg aaaactcctg gacaatcagt aaagagtacc atattgatga agaagtgggc     180
tttgctctgc caaatccaca ggaaaatcta cctgattttt ataatgactg gatgttcatt     240
```

```
gctaaacatc tgcctgatct catagagtct ggccagcttc gagaaagagt tgagaagtta        300
aacatgctca gcattgatca tctcacagac cacaagtcac agcgccttgc acgtctagtt        360
ctgggatgca tcaccatggc atatgtgtgg ggcaaaggtc atggagatgt ccgtaaggtc        420
ttgccaagaa atattgctgt tccttactgc caactctcca agaaactgga actgcctcct        480
attttggttt atgcagactg tgtcttggca aactggaaga aaaaggatcc taataagccc        540
ctgacttatg agaacatgga cgttttgttc tcatttcgtg atggagactg cagtaaagga        600
ttcttcctgg tctctctatt ggtggaaata gcagctgctt ctgcaatcaa agtaattcct        660
actgtattca aggcaatgca aatgcaagaa cgggacactt tgctaaaggc gctgttggaa        720
atagcttctt gcttggagaa agcccttcaa gtgtttcacc aaatccacga tcatgtgaac        780
ccaaaagcat ttttcagtgt tcttcgcata tatttgtctg gctggaaagg caaccccag         840 ctatcagacg gtctggtgta tgaagggttc tgggaagacc caaggagtt tgcagggggc         900 agtgcaggcc aaagcagcgt cttt cagtgc tttgacgtcc tgctgggcat ccagcagact       960
gctggtggag gacatgctgc tcagttcctc caggacatga gaagatatat gccaccagct      1020
cacaggaact tcctgtgctc attagagtca aatccctcag tccgtgagtt tgtcctttca      1080
aaaggtgatg ctggcctgcg ggaagcttat gacgcctgtg tgaaagctct ggtctccctg      1140
aggagctacc atctgcaaat cgtgactaag tacatcctga ttcctgcaag ccagcagcca      1200
aaggagaata agacctctga agacccttca aaactggaag ccaaaggaac tggaggcact      1260
gatttaatga atttcctgaa gactgtaaga agtacaactg agaaatccct tttgaaggaa      1320
ggttaatgta acccaacaag agcacatttt atcatagcag agacatctgt atgcattcct      1380
gtcattaccc attgtaacag agccacaaac taatactatg caatgttta ccaataatgc       1440 aatacaaaag acctcaaaat acctgtgcat ttcttgtagg aaaacaacaa aaggtaatta      1500
tgtgtaatta tactagaagt tttgtaatct gtatcttatc attggaataa aatgacattc      1560
aataaataaa aa                                                           1572
```